US009931316B2

(12) United States Patent
Stamets

(10) Patent No.: US 9,931,316 B2

(45) Date of Patent: Apr. 3, 2018

(54) ANTIVIRAL ACTIVITY FROM MEDICINAL MUSHROOMS AND THEIR ACTIVE CONSTITUENTS

(71) Applicant: Paul Edward Stamets, Shelton, WA (US)

(72) Inventor: Paul Edward Stamets, Shelton, WA (US)

(*) Notice: Subject to any disclaimer, the term of this patent is extended or adjusted under 35 U.S.C. 154(b) by 0 days.

(21) Appl. No.: 14/853,932

(22) Filed: Sep. 14, 2015

(65) Prior Publication Data

US 2016/0000754 A1 Jan. 7, 2016

Related U.S. Application Data

(60) Provisional application No. 62/140,459, filed on Mar. 31, 2015.

(51) Int. Cl.

| | |
|---|---|
| *A61K 31/37* | (2006.01) |
| *A61K 31/05* | (2006.01) |
| *A61K 31/12* | (2006.01) |
| *A61K 31/192* | (2006.01) |
| *A61K 31/352* | (2006.01) |
| *A61K 31/7048* | (2006.01) |
| *A61K 36/06* | (2006.01) |
| *A61K 36/07* | (2006.01) |
| *A61K 36/074* | (2006.01) |

(52) U.S. Cl.

CPC .............. *A61K 31/37* (2013.01); *A61K 31/05* (2013.01); *A61K 31/12* (2013.01); *A61K 31/192* (2013.01); *A61K 31/352* (2013.01); *A61K 31/7048* (2013.01); *A61K 36/06* (2013.01); *A61K 36/07* (2013.01); *A61K 36/074* (2013.01)

(58) Field of Classification Search

CPC ...... A61K 31/37; A61K 31/192; A61K 31/12; A61K 31/352; A61K 31/7048; A61K 31/05; A61K 36/06

USPC ........................... 514/27, 456, 457, 568, 570

See application file for complete search history.

(56) References Cited

U.S. PATENT DOCUMENTS

| | | | | |
|---|---|---|---|---|
| 9,474,776 B2 | 10/2016 | Stamets | | |
| 2009/0130138 A1 | 5/2009 | Stamets | | |
| 2010/0178364 A1* | 7/2010 | Polansky | .............. | A61K 31/11 424/702 |

FOREIGN PATENT DOCUMENTS

| | | |
|---|---|---|
| NL | 2009671 | * 4/2014 |

OTHER PUBLICATIONS

Glossary of medical education terms, Institute of International Medical Education. http://www.iime.org/glossary.htm Accessed in Mar. 2013.*

Chattopadhyay et al. Ethnomedicines for the development of anti-herpesvirus agents. Research Signpost pp. 117-147, 2010.*

Hwang et al. Chlorinated Coumarins from the Polypore Mushroom Fomitopsis off icinalis and Their Activity against *Mycobacterium tuberculosis*. J Nat Prodt 76:1916-1922, 2013.*

Davy et al. Total blood volume in healthy young and older men. J. Appl. Physiol. 76(5):2059-2062, 1994.*

Awadh Ali et al. Antiviral activity of Inonotus hispidus. Fitoterapia 74:483-485, 2003.*

Khan G. Epstein-Barr virus, cytokines, and inflammation: A cocktail for the pathogenesis of Hodgkin's lymphoma? Experimental Hematology 34:399-406, 2006.*

Ravindran et al. Bisdemethylcurcumin and structurally related hispolon analogues of curcumin exhibit enhanced prooxidant, anti-proliferative and anti-inflammatory activities in vitro. Biochemical Pharmacology 79:1658-1666, 2010.*

Lyu et al. Antiherpetic Activities of Flavonoids against Herpes Simplex Virus Type 1 (HSV-1) and Type 2 (HSV-2) In Vitro. Arch Pharm Res vol. 28, No. 11, 1293-1301, 2005.*

Chiang et al. Antiviral activity of Plantago major extracts and related compounds in vitro. Antiviral Research 55 (2002) 53-62.*

N.A. Awadh Ali et al, Antiviral activity of Inonotus hispidus, Fitoterapia, Jul. 1, 2003, pp. 483-485, vol. 74, No. 5.

Jianmin Wang et al., Anti-Enterovirus 71 Effects of Chrysin and Its Phosphate Ester, PLOS ONE, Mar. 5, 2014, p. e89668, vol. 9, No. 3.

M.J Alves et al., Antimicrobial activity of phenolic compounds identified in wild mushrooms, SAR analysis and docking studies, Journal of Applied Microbiology, Aug. 1, 2013, pp. 346-357, vol. 115(2).

Chang Hwa Hwang et al., Chlorinated Coumarins from the Polypore Mushroom Fomitopsis officinalis and Their Activity against *Mycobacterium tuberculosis*, Journal of Natural Products, Oct. 25, 2013, pp. 1916-1922, vol. 76, No. 10.

Drach et al., The selective inhibition of viral DNA synthesis by chemotherapeutic agents: an indicator of clinical usefulness?, Mar. 4, 1977, pp. 396-409, vol. 284.

Martinez et al., Antiviral drug discovery: broad-spectrum drugs from nature, Jan. 2015, Natural Products Reports, pp. 29-48, vol. 32(1).

Tamargo et al., Narrow therapeutic index drugs: a clinical pharmacological consideration to flecainide, European Journal of Clinical Pharmacology, 2015, 549-567, vol. 71.

Muller et al., The determination and interpretation of the therapeutic index in drug development, Nature Reviews Drug Discovery, Oct. 2012, pp. 751-761, vol. 11.

Unknown, Guidance for Industry Antiviral Product Development—Conducting and Submitting Virology Studies to the Agency, U.S. Department of Health and Human Services, Food and Drug Administration, Center for Drug Evaluation and Research (CDER), Jun. 2006, pp. 1-14.

(Continued)

*Primary Examiner* — Yih-Horng Shiao

(74) *Attorney, Agent, or Firm* — William R. Hyde; Bernard A. Brown, II

(57) ABSTRACT

Compounds having unique antiviral properties found in mushroom mycelium and their analogs are extracted, concentrated, isolated or manufactured to create compositions useful in preventing the spread and proliferation of various viruses afflicting animals, particularly viruses harming humans, pigs, birds, bats and bees. Such compounds and compositions can be used individually or in combination with known medicines or natural products to improve health.

10 Claims, No Drawings

(56) References Cited

OTHER PUBLICATIONS

Badisha et al., Selective Cytotoxic Activities of Two Novel Synthetic Drugs on Human Breast Carcinoma MCF-7 Cells, Anticancer Research, 2009, pp. 2993-2996, vol. 29.
Roth et al., A recombinant, infectious human parainfluenza virus type 3 expressing the enhanced green fluorescent protein for use in high-throughput antiviral assays, 2009, Antiviral Research, pp. 12-21, vol. 82.

* cited by examiner

ANTIVIRAL ACTIVITY FROM MEDICINAL MUSHROOMS AND THEIR ACTIVE CONSTITUENTS

CROSS-REFERENCE TO RELATED APPLICATIONS

This application claims the benefit of U.S. Provisional Application No. 62/140,459, filed Mar. 31, 2015, which is hereby incorporated by reference in its entirety.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

BACKGROUND OF THE INVENTION

1. Field of the Invention

The present invention relates to antiviral compositions based upon constituents isolated from or contained within medicinal mushroom mycelia, or the corresponding synthetic molecules, that are shown to be useful in reducing pathogenic viruses, and treating viral infections; in particular viruses that afflict animals, including, but not limited to, humans, bees, pigs, bats, and birds, resulting in a reduction of disease causing viruses, their pathogenicity and/or infectivity in both the animal host and the environment.

2. Description of Related Art Including Information Disclosed Under 37 CFR 1.97 and 1.98

Medicinal mushrooms have been used for thousands of years for a wide assortment of ailments. Traditionally the mushroom fruitbody has been used. Scientists have extensively studied extracts of the fruitbodies over the past decades. Although numerous papers have been published showing hot water extracts of mushrooms and their mycelia can activate immune systems and can be anti-inflammatory, comparatively few have elucidated the benefits of the alcohol fractions. The current invention describes novel contributions to the field of medicinal mushroom research, particularly discoveries pertaining to antiviral activity of alcohol extracted mushroom mycelium and the active constituents contained within them.

Scientists are now discovering that viral infection challenges and degrades the immune system in multiple ways including inflammation, which can lead to cellular damage from free radicals, a cofactor in carcinogenesis, and to cancers caused by oncoviruses. Worldwide, the World Health Organization (WHO) International Agency for Research on Cancer estimated that in 2002 17.8% of human cancers were caused by infection, with 11.9% being caused by 1 of 7 different viruses. The 7 viruses that are known to cause cancer include three herpes oncoviruses: Epstein-Barr aka human herpesvirus 4 (HHV-4); human herpesvirus 6 (HHV-6) and human herpesvirus 8 (HHV-8). HHV-6 is implicated in the development of lymphomas, leukemia, cervical cancers, Karposi sarcoma, and brain tumors. Other oncoviruses include the polyoma virus that causes Merkel cell carcinoma (MCC), the human papillomaviruses (HPV 16 and 18) which cause cervical cancer, anal cancer, oropharyngeal cancers, vaginal cancers, vulvar cancers and penile cancers; hepatitis B and C, which cause liver cancer; and the human T-lymphotropic viruses (HTLV), which cause T-cell leukemia and T-cell lymphoma. Four HTLVs are well known. HTLV-1 and HTLV-2 are involved in epidemics, infecting 15-20 million people worldwide. In the United States, hepatitis C infection is estimated at 2.7 million and 700,000-1.4 million persons are estimated to be infected with hepatitis B. HTLVs can be more prevalent in some geographical regions than others, infecting around 1% of Japan's population. Rates among volunteer blood donors in the U.S. average 0.016% but in parts of Africa, reports of 15% have been recorded.[1]

As science progresses, more oncoviruses and virally-mediated oncogenic pathways are likely to be discovered. Since immunity is based on many complex factors, pathogenic viruses which have not been known to specifically cause cancer may contribute to carcinogenesis by causing inflammation, free radicals, and reducing the number of immune cells that would otherwise keep cancer and co-infections at bay. Nature is a number's game, and the balance between health and disease is imperiled by infections. When immunity is lowered, the human body is less able to eradicate cancer cells, which would otherwise be kept in check, and deleterious inflammatory pathways further challenge health. Thus mortality rates rise with compounded infections. Hence there is a need for compositions that reduce oncoviruses and also reduce viruses that cause inflammation and immune deactivation, contributory to oncogenesis.

Viral epidemics and pandemics represent increasing threats to global health as zoonotic diseases spread, jumping host species, recombining, and potentially mutating into more virulent forms. The need for additional anti-influenza drugs is important in maintaining active countermeasures against pandemics. As an example, when H1N1 flu virus swept the world in 2010, the two most popularly effective antivirals were Tamiflu® (Oseltamivir) and Relenza® (Zanamivir); which were useful, at best, for shortening the disease period by approximately a day. In less than one year, the novel H1N1 virus evolved to increasingly resist Tamiflu® applications, and the drug has largely become ineffective against downstream populations of the heritage H1N1 swine flu viruses. Although some antiviral medicines may be effective at present, it is vital that researchers investigate diverse therapeutic agents in order to combat viral outbreaks from rapidly evolving strains. The ease and speed with which numerous varieties of flu virus mutate to become drug resistant is particularly concerning.

In the spring of 2015, wild birds from Asia carried H5N8 viruses to North America, which co-mingled with bird flu variants and mutated into a highly pathogenic H5N2 virus. This virus resulted in the killing—both from the virus and euthanasia—of tens of millions of birds and threatened the multibillion dollar chicken and turkey industry. The H5N2 virus has mutated into H5N1 variants, and given the number of hosts in wild and domesticated birds, continued mutations could evolve a strain of the flu that could leap to humans, causing a pandemic and severe devastation to our global economies, our food biosecurity and human health. Given that flu viruses can be spread via airborne, direct and secondary contacts (via vehicles, shoes, clothing, washcloths, dollar bills, flies, mites, etc.) and that flu viruses can survive in mucous droplets for up to 17 days, the threat of a flu pandemic spreading to humans greatly concerns specialists in virology, public health and defense. Finding methods and compositions to reduce the viral pathogen payloads vectored by host animals and fomites will greatly serve the public interest. Moreover, since most vaccines have limited (but focused) utility against only a few flu variants, finding broad based solutions to preventing and reducing the threat from multiple flu viruses in particular, and diverse viruses in general, is of paramount importance.

Medicinal mushrooms have been ingested as food and as therapy for hundreds, and in some cases, thousands of years. This is strong support for their safe ingestion, making them appealing candidates in the search for new antiviral agents. In addition, the compounds disclosed herein may be resident ingredients within well-known foods, which, when isolated and concentrated can function as drugs. The difference here then between a food and a drug is that a drug is typically an isolated molecule presented in a form at a high purity (i.e. >90%), and used at a high dose in treating a disease. One of the first mushrooms recognized for its antiviral activity was *Fomes fomentarius*, a hoof-shaped wood conk that was found to inhibit the tobacco mosaic virus.[2] More recently, derivatives of the Gypsy mushroom, Rozites caperata, were found by Piraino et al. to significantly inhibit the replication and spread of varicella zoster (the 'shingles' virus), influenza A and B, and herpes simplex I and II. Sarkar et al. have also identified activity against herpes simplex I in an extract of Shiitake mushrooms (*Lentinula edodes*).[3,4] Collins and Ng have identified a polysaccharopeptide inhibiting HIV type 1 infection from Turkey Tail mushrooms (*Coriolus versicolor=Trametes versicolor*).[5] Brandt and Piraino, and Stamets have also published summaries of the antiviral properties of some mushrooms species.[6,7]

The prevailing adamant belief by those skilled in the science of medicinal mushroom research is that the only benefits from medicinal mushroom extracts must come from hot water extraction. As three noted experts, skilled in the art, and authors of scientific papers and books on the medicinal properties of mushrooms, have published: "Hot water extracts are the only form of mushroom preparation ever used in Traditional Chinese Medicine (TCM), and the only form of mushroom supplement ever used, tested or studied in the scientific and medical research." (The Health Benefits of Medicinal Mushrooms, 2005, Dr. Mark Stengler).[8]

According to John Seleen of Mushroom Science (currently on his Mushroom Science website), "Few people realize how much research has been conducted on medicinal mushrooms; more than 2,000 studies have been published in just the last 10 years, and all of these studies have used hot water extracts. In fact, hot water extracts are the only type of medicinal mushroom preparation that has actual proof of effectiveness for supporting immune health . . . . It is not often that you have absolute consensus between 1,000's of years of herbal practice and every scientific study ever published on that same subject, but that is the case with medicinal mushrooms. All sources and traditions agree, medicinal mushrooms must be extracted with hot water when used for immune support, and hot water extracts are the only type of mushroom supplement validated by the research." (Sep. 10, 2015).

Additionally, a 2015 'white paper' by Jeffery S. Chilton, *Redefining Medicinal Mushrooms: A new scientific screening program for active compounds* states that if mycelium is grown on rice, and not wood, that "Without the natural precursors, basidiomycete mycelium in sterile culture produces few of the important secondary metabolites." Thus these three experts, skilled in the art, and greatly influential, are unanimous in discrediting any significant activity of non-hot water mycelial extracts, especially when mycelium is grown on grains such as rice. Thus they teach away from the specifics of this invention.

With the advent of tissue culture of mycelium in the early part of the 20th century, this new mushroom life stage (the mycelium as opposed to the mushroom fruit bodies) became available for testing bioactivity. This newly available fungal form opened up new frontiers for natural product research. However, pharmaceutical companies studying mushroom-based natural products, typically and more inexpensively, analyze the fruitbodies, and in doing so miss the antiviral activities this inventor has discovered that are expressed during the mycelium life stage.

From a practical point of view, pharmaceutical researchers find it easier to collect and analyze a mushroom rather than to laboriously culture it and then analyze the mycelium. This standard approach has a reasonable rationale: many species of mushroom forming fungi do not grow, or are too slow to grow in in vitro culture compared to other fungi such as molds. Additionally, the mushroom fruitbodies are made of compacted mycelium—dense with tissue—and hence would seemingly be a better resource for bioprospecting than the more loosely netted mycelium. This would explain why there is little prior art on the mycelium of mushroom species being anti-virally active. Typically, when a pharmaceutical company screens mushroom-based natural products, they analyze large sets of species. If they do not find activity in the natural form (the mushroom fruitbody or carpophore), they move on to other species without further exploring a negative result, based upon the mistaken belief that the activities of the mushrooms would be the same as the mycelium and that all strains or cultivars of a species would possess the same antiviral activity. This is understandable since the prevailing belief is that the mushroom is simply composed of compacted mycelium and the two would share, in common, the same constituents.

Recent genomic research shows that more genes are turned on during the mycelial stage of development than in the reproductive structure of the mushroom fruitbodies. As was noted by Li et al., 2013, "The protein-coding genes were expressed higher in mycelia or primordial stages compared with those in the fruiting bodies."[9] The inventor's practices have inadvertently laid claim to or supported this statement without prior knowledge that more genes are up-regulated during mycelial growth than fruitbody (mushroom) formation. This was not known, nor obvious, at the time when this patent applicant filed his first provisional antiviral patent application U.S. 60/534,776 on Jan. 6, 2004.

Remarkably, and unexpectedly, the author's discovery that the alcohol soluble extracts of *Ganoderma lucidum* (*Ganoderma lucidum* var. *resinaceum*) mycelium showed anti-flu activity is novel in that it is in direct contradiction to past results that alcohol extracts from fruitbody extracts had no activity. This is unique in that it is counter-intuitive as conventional thinking would lead most scientists to believe that the activity of both forms would share commonality of effects.

Seong-Kug Eo tested both water soluble and alcohol soluble fractions from the fruitbodies of *Ganoderma lucidum*.[10] The methanol soluble compounds were labeled as "GLMe," for "*Ganoderma lucidum* methanol fraction" and "GLhw" for "*G. lucidum* hot water."—Their conclusions showed that the methanol (alcohol) soluble fractions had no activity against flu viruses: "The carpophores of *G. lucidum* (500 g) were disrupted and extracted with hot water for 8 h. The water extract was concentrated to a 10th of the original volume, and three volumes of ice cold EtOH added to precipitate the high molecular weight components. After standing out overnight at 4° C., it was centrifuged and the precipitates were lyophilized, and GLhw (3.30 g) as a brownish substance was obtained. Eight methanol soluble substances (GLMe) were isolated by organic solvents on the basis of differences in the net electric charge. GLMe-1, -2, -4 and -7 isolated from the MeOH fraction exhibited inhibitory effects, especially on the cytopathic effects induced by VSV Indiana and New Jersey strains at concentrations which did not show cytotoxicity against Vero cells; however, they exhibited no effect on the other viruses such as HSV and influenza A virus."

The author notes that this article has been referenced, as of this date, Aug. 18, 2015, 2,090 times according to Google and 3,570 times by Bing search engines, showing that Seong-Kug Eo et al.'s (1999) statement that the alcohol soluble fractions of *Ganoderma lucidum* were inactive against flu and herpes viruses was well established in the scientific literature.

This discovery by Seong-Kug Eo et al. (1999) teaches away from Stamets U.S. Pat. No. 8,765,138 (2014), the latter of which discloses that alcohol extracts of the *Ganoderma lucidum* mycelium were highly active against flu and herpes viruses. Conventional wisdom has been that the fruitbodies (mushrooms) of *Ganoderma lucidum* held the most diverse bioactive constituents and that the mycelium is less active. Moreover, since the fruitbodies are composed of mycelium, that there would be differences between extracts made from mushrooms vs mycelia would have been seen, by those currently and historically skilled in preparations of mushrooms, to be a factual contradiction. Hence, the inventor's results were both novel and nonobvious at the time of this inventor's first antiviral patent applications wherein he found that the EtOH/H2O extracts of fruitbodies of Agarikon (*Fomitopsis officinalis*) were inactive against pox, flu and herpes viruses whilst the EtOH/$H_2O$ extracts from the living mycelium of this species were active against the same viruses.

BRIEF SUMMARY OF THE INVENTION

In view of the lack of use of medicinal mushroom mycelium and its inherent components to protect against viruses afflicting animals, the present invention provides novel compositions and methods of using such agents or their cheaper synthetic equivalents.

The present invention offers a unique approach to viral control by utilizing molecular constituents, more specifically discrete active pharmacological ingredients, resident within aqueous-ethanol extracts from the living mycelium of *Antrodia, Fomes, Fomitopsis, Ganoderma, Inonotus, Schizophyllum, Phellinus, Piptoporus, Trametes* and other taxa in the Polyporaceae, and a range of active principle ingredients coded by gene sequences from the mycelia of related medicinal mushrooms to combat harmful viruses.

This patent focuses on EtOH/$H_2O$ (ethyl alcohol/water) extracts from living mycelium to discover new medicines, particularly antivirals. Methanol, and other solvents known to the art can be used but the inventor focused on ethanol because ethanol can be consumed whereas methanol is highly toxic (causing blindness) if consumed. New antiviral molecules are disclosed that are components within the extracts of living mycelium.

Hence this invention not only provides the first evidence that extracts and molecules within these extracts reduce some oncoviruses and also reduce viruses that cause inflammation and immune deactivation, contributory to oncogenesis. Not only do these extracts and active constituents reduce the pathogenicity of viruses but reduce also, as a consequence, cancer risk. Therefore the active agents found by this inventor can be combined for anticancer compositions, significantly enhancing the benefits of other anticancer drugs and integrative medicine programs for increasing the quality of life of cancer patients.

This invention offers a broad bioshield of defense from pathogenic viruses for humans, birds, bees, pigs, and other animals using extracts from medicinal mushrooms and their active molecules. These extracts contain many antiviral compounds, the use of which is new to science, unanticipated and nonobvious.

The inventor surveyed the scientific literature up to 2001 and wrote a literature review for the peer-reviewed journal HerbalGram.[11] The antivirals from mushroom species—up to that date—were made from fruitbody extracts, except in the case of Shiitake (LEM from *Lentinula edodes*) and Turkey Tail (PSP and PSK from *Trametes versicolor*). LEM, PSP and PSK are isolated using hot water as the primary, "first step" extracting solvent. Noteworthy is that LEM, PSK and PSP precipitate out of solution when EtOH levels exceed 25-35%—a method this inventor practices. Using the clarified supernatant, devoid of the precipitant rich LEM, PSK and PSP compounds, this inventor opposed conventional thinking. Removal of ethanol insoluble beta-glucans and proteins, helped, in this inventor's opinion, unmask a new set of antiviral agents. However, the inventor, in 2001, reflecting the current conventional wisdom of the science stated in the inventor's peer reviewed botanical journal article[12] that the only antivirals known are from hot water extraction and these are polysaccharide or polysaccharide protein rich (beta-glucan) based antivirals present both in the mycelium and in the fruiting bodies. As it turns out, this was not necessarily true, as was subsequently discovered by this inventor, much to his surprise, and contrary to conventional wisdom to those skilled in the art.

DETAILED DESCRIPTION OF THE INVENTION

The invention includes active principle ingredients found in the combination of products from the mycelia of multiple mushroom species in a form to have the accumulated effect of restricting the growth, spread and survivability of viruses in animals, especially humans, birds and bees. The present invention also includes the combination of products from multiple mushroom species in a form useful for preventing, treating, alleviating, mitigating, ameliorating or reducing viruses, including oncoviruses, in animals including humans. Such forms may have the additional advantages of functioning as antibacterials, antiprotozoals, immunomodulators, nutraceuticals and/or prebiotics as well as enhancing innate immunity defense mechanisms and host immune response, resulting in healing.

Mushrooms exhibiting medicinal properties are numerous. Some species and subspecies ("strains") vary in their proportionalities of constituents. This inventor has found a surprising array of antiviral molecules spread amongst different families of molecules. More particularly, polyphenols within the polyporales (the so called 'polypore' mushrooms) contain many of the antiviral molecules discovered by this inventor, many of which are expressed as extracellular, primary and secondary metabolites. These molecules are variously soluble in a wide range of solvents, from highly polar water to hexane and oils, which are least polar. The polyphenols, lipids and fatty acids of greatest interest for novel antiviral activity are particularly, but not exclusively, those that are soluble in non-polar solvents.

The aqueous-alcohol extracts of antiviral and antibacterial mushroom mycelia, especially in the polyporaceae, more specifically *Fomitopsis officinalis* (=*Laricifomes officinalis*), *Fomitopsis pinicola, Ganoderma annulare, Ganoderma lingzhi, Ganoderma lucidum, Ganoderma lucidum* var. *resinaceum* (=*Ganoderma resinaceum*), *Ganoderma applanatum, Ganoderma brownii, Ganoderma atrum, Ganoderma oregonense, Ganoderma sinense, Ganoderma tsugae*, and *other Ganoderma* species, *Inonotus obliquus, Piptoporus betulinus, Schizophyllum commune*, and *Trametes versicolor* contain molecules highly active in reducing pathogenic viruses. Additional species likely to provide a reservoir of antiviral molecules include but are not limited to Polyporales and Hymenochaetales such as *Antrodia cinnomonea, Fomitiporia robusta, Fomes fomentarius, Ganoderma curtisii, Ganoderma lingzhi, Grifola frondosa, Heterobasidion annosum, Inonotus hispidus, Inonotus andersonii, Inonotus dryadeus, Irpex lacteus, Laetiporus cincinnatus, Laetiporus sulphureus, Laetiporus conifericola, Lentinula edodes, Lenzites betulina, Phanerochaete chrysosporium, Phaeolus schweinitzii, Phellinus baumii, Phellinus igniarius, Phellinus linteus, Phellinus pini, Polyporus elegans, Phanerochaetes chrysosporium, Phaeolus schweitnitzii, Stereum complicatum, Stereum hirsutum, Stereum ostrea, Trametes elegans, Trametes gibbosa, Trametes hirsuta, Trametes villosa, Trametes cingulata, Trametes ochracea, Trametes pubescens, Trametes ectypa, Trametes aesculi, Wolfiporia cocos*, and Agaricales such as *Agaricus augustus, Agaricus blazei, Agaricus bonardii, Agaricus brasiliensis, Agaricus campestris, Agaricus lilaceps, Agaricus placomyces, Agaricus subrufescens, Agaricus sylvicola, Agrocybe pediades, Agrocybe aegerita, Agrocybe arvalis, Agrocybe praecox, Amanita muscaria, Amanita gemmata, Amanita pantherina, Amanita phalloides, Amanita virosa, Amanita pachycolea, Amanita vaginata, Clitocybe odora, Clitocybe dealbata, Clitocybe dilitata, Conocybe cyanopus, Conocybe lacteus, Conocybe rickenii, Conocybe smithii, Conocybe tenera, Coprinopsis atrementaria, Coprinopsis nivea, Coprinopsis lagopus, Coprinus comatus, Coprinus micaceus, Galerina autumnalis, Galerina marginata, Galerina venenata, Gymnopus hydrophilus, Gymnopilus peronatus, Hypholoma aurantica* (*Leratiomyces ceres*), *Hypholoma capnoides, Hypholoma fasciculare, Hypholoma sublateritium, Hypsizygus marmoreus, Hypsizygus tessulatus, Hypsizygus ulmarius, Lentinus ponderosus, Lepiota procera* (*Macrolepiota procera*), *Lepiota rachodes* (*Chlorophyllum rachodes*), *Lepista nuda, Mycena alcalina, Mycena pura, Mycena aurantiadisca, Panellus serotinus, Panaeolus foenisecii, Panaeolus subbalteatus, Pleurotus columbinus, Pleurotus ostreatus, Pleurotus cystidiosus, Pleurotus pulmonarius, Pleurotus sapidus, Pleurotus tuberregium, Panellus stipticus, Panellus serotinus, Pluteus cervinus, Psathyrella aquatica, Psathyrella condolleana, Psathyrella hydrophila, Psilocybe allenii, Psilocybe azurescens, Psilocybe baeocystis, Psilocybe caerulescens, Psilocybe coprophila, Psilocybe cubensis, Psilocybe cyanescens, Psilocybe ovoideocystidiata, Psilocybe semilanceata, Psilocybe stuntzii, Psilocybe subaeruginosa, Psilocybe weilii, Stropharia aeruginosa, Stropharia coronilla, Stropharia coronilla, Stropharia cyanea, Stropharia rugoso-annulata, Stropharia semiglobata, Stropharia semigloboides, Stropharia squamosa, Stropharia thrausta, Stropharia umbonotescens, Termitomyces robusta, Volvaria bombycina, Volvariella volvacea, and ascomycetes such as Metarhizium anisopliae, Metarhizium acridum, Beauveria bassiana, Cordyceps capitata, Cordyceps militaris, Cordyceps sinensis sensu lato, Cordyceps subsessilis, Ophiocordyceps sinensis*, and *Ophiocordyceps unilateralis.*

The effect of the antiviral and antibacterial components within the aforementioned mushroom species and their relatives may be the decisive factor that improves survivability from infection in many animals including humans, dogs, cats, horses, cows, pigs, birds, fish, insects (including bees) and other wild and domesticated animals. Moreover, these mushroom extracts, and natural or synthetic versions of the compounds contained in such extracts, can enhance and be combined with a wide range of conventional anticancer therapies, including chemotherapies using herceptin, tamoxifen, taxol, interferon alpha, as well as vaccines, gene therapies, including incorporating nanobots, radiological, immunological, sonic, photonic, electrical, cold shock, electromagnetic, and microbiomic and other cancer therapies.

Lowering the cancer-causing effects of viruses and bacteria are a consequence of and are derived from the antiviral, antibacterial and other medicinal effects of polypore mushroom mycelia in particular, and the mycelia from other medicinal mushrooms in general, as described in U.S. Pat. No. 8,765,138, issued Jul. 1, 2014 by the inventor. By employing extracts and the derivative active ingredients from these antiviral and antibacterial fungi, improvement in survivability of patients can be significantly realized.

Methods of Extraction

This inventor has discovered that cold water or ambient temperature (75° F.≈24° C.) EtOH/$H_2O$ (ethanol/water) extractions as outlined in U.S. Pat. No. 8,765,138 (2014) and U.S. patent application Ser. No. 14/641,432 (2015), are effective for extracting high potency antiviral molecules and are immune supporting, contrary to prevailing opinions of experts skilled in the art who argue that only hot water extracts are useful for extracting medicinal mushroom-based immune supporting compounds.

In contrast, the inventor discovered that cold extraction yielded antiviral actives contrary to conventional thinking, which advocates hot extraction. "Cold" is an empirical perception. The inventor defines "cold" as being <98.6° F. (<37° C.) the average temperature of a human and "hot" as being >98.6° F. (>37° C.). The inventor used cold extraction methods, more specifically at room temperature (≈72-75° F.; ≈22-24° C.), to make ethanol/water extracts of the mycelium of *Fomitopsis officinalis*, which in turn showed strong activity against flu, herpes and pox viruses whereas cold water and hot water extracts >180° F. (82° C.) from the fruitbody of the same strain showed no activity against these same viruses.

Moreover, the inventor focuses on using mycelium, not fruitbodies, from traditionally used medicinal macrofungi in the discovery of powerful antiviral properties and structures. This inventor has identified numerous antiviral molecules resident within and expressed extracellularly by the mycelium and extractable with cold water/ethanol, from grain (rice), wood, and lignocellulosic based substrates, using solvents other than hot water to create novel compositions useful for reducing viruses and their cross infectivity to help animal cells from viral invasion and replication.

Optimizing dosage is dependent upon numerous variables. The difference between a medicine and poison is often dosage. Determining the proper dose for antiviral effects will only require routine experimentation because the concentrations of extracts can be simply diluted or concentrated by adjusting ethanol and/or water content. In general, with regard to *Ganoderma lucidum* var. *resinaceum* ("G.r.") blends, compositions consisting of 5-95% G.r. are preferred, 10-75% is more preferred and 20-50% is most preferred.

The term "effective amount" refers to an amount sufficient to have antiviral activity and/or enhance a host defense mechanism as more fully described below. This amount may vary to some degree depending on the mode of administration, but will be in the same general range. The exact effective amount necessary could vary from subject to subject, depending on the species, preventative treatment or condition being treated, the mode of administration, etc. The appropriate effective amount may be determined by one of ordinary skill in the art using only routine experimentation or prior knowledge in the art in view of the present disclosure.

The average American adult has increased body mass compared to the past, hence a dosage regimen must account for larger individuals than has been historically practiced. For instance, the average American woman weighed 142 (64.4 kg) lbs in 1990; today, the average woman weighs 160 lbs (72.6 kg). Similarly the average weight for American men in 1990 was 180 lbs, (81.6 kg) and today men average around 195 lbs (88.4 kg). By way of an example, a typical dosage regimen for adults of varying body mass, could be calculated at follows, allowing for considerable flexibility of dosages depending on circumstances known to the science of pharmaceutical dosing.

Typical therapeutic amounts of mycelium grown on rice for a 180 lbs (81.6 kg.) adult, (extracts of individual fungal species and/or combinations of species) are preferably 0.1-20 g/day, more preferably 0.25-10 g/day, and most preferably 0.5-5 g/day.

Typical therapeutic amounts of extracts (individual fungal species and/or combinations of species) preferably deliver 0.1-20 mg extracted materials per kg of body weight, more preferably 0.25-10 mg/kg of body weight and most preferably 0.5-5 mg/kg of body weight.

Typical daily dose therapeutic amounts of active molecules or active principal ingredients, including ethyl 7-chloro-2-oxo-4-phenyl-2H-chromen-3-carboxylate, vanillic acid, hispolon, quercetin hydrate, rutin hydrate, syringic acid, trans-cinnamic acid, trans-ferulic acid and conjugate and ionic salts of vanillic acid, syringic acid, trans-cinnamic acid and trans-ferulic acid, for prevention of viral infection preferably range from about 100-200 mg daily (about 1.2-2.4 mg/kg of body weight for a 180 lbs or 81.6 kg adult), preferably divided into two dosage units administered twice per day. A preferred daily therapeutic dose is about 200 mg. Typical therapeutic amounts of active molecules or active principle ingredients for treating, ameliorating, mitigating, alleviating, reducing and curing a pathogenic virus infection preferably range from about 0.001 to 2.0 g/day, more preferably range from about 0.1 to 1.5 g/day and most preferably range from about 0.25 to 1.4 g/day, preferably divided into two dosage units administered twice per day for a period of time ranging from 10 to 60 days. A preferred daily therapeutic dose for treating a pathogenic viral infection is about 1,000 mg subject to adjustments for weight as above. Typical therapeutic amounts of active ingredients preferably deliver about 0.012 mg to 24.5 mg active ingredient per kg of body weight based on an average body weight of 180 lbs (81.6 kg), more preferably about 1.2 mg to 18.4 mg/kg of body weight and most preferably about 3.1 to 17.2 mg/kg of body weight. A preferred daily therapeutic dose for the potential use of psilocin would be about 0.1 mg per kg of body weight.

Body Weight, Daily Dose and Number of Capsules

| Body Weight kg (lbs) | Daily Dose | Number of Capsules |
|---|---|---|
| <66 | 800 mg/day | 2 x 200-mg capsules A.M. |
| (<144) | | 2 x 200 mg capsules P.M. |
| 66-80 | 1000 mg/day | 2 x 200-mg capsules A.M. |
| (145-177) | | 3 x 200-mg capsules P.M. |
| 81-105 | 1200 mg/day | 3 x 200-mg capsules A.M. |
| (178-231) | | 3 x 200-mg capsules P.M. |
| >105 | 1400 mg/day | 3 x 200-mg capsules A.M. |
| (231) | | 4 x 200-mg capsules P.M. |

Note that effective ranges/dosages are not expected to be precisely the same for all compounds. Dosages may be optimized with each compound when the pharmacokinetics are studied to see how each compound is metabolized in the gastrointestinal tracts and in the liver through the cytochrome P450 pathways, which may alter the dose ranges. However, these compounds were compared side-by-side to well-studied antiviral drugs within the same dosage ranges recognized by pharmaceutical science, so these dosage levels are predictive and rational.

Delivery systems of these compositions containing one or a plurality of antiviral molecules include, but are not limited to: sprays, capsules, tablets, elixirs, emulsions, lozenges, suspensions, syrups, pills, lotions, epidermal patches, suppositories, inhalers, and injectables, or by other means known to the art of drug delivery. For measured, long term dosing and to achieve a more consistent effect, delayed release delivery systems known to the pharmaceutical industry can be employed. Additionally, these compounds can be combined with other drugs or enzyme suppressants to allow passage through the liver's complex cytochrome P450 and related pathways to yield an effective amount into the blood stream.

The antiviral extracts, active constituents, mycelium and/or other derivatives may be incorporated into foods to produce foods with antiviral properties, useful for protecting animals including humans, dogs, cats, horses, cows, pigs, birds, fish, insects, including bees, and other wild and domesticated animals, from infection.

To the best of this inventor's knowledge, it is unprecedented to have an antiviral extract dually active against viruses that infect humans and viruses that infect honey bees. That the alcohol-water extracts of polypore mushrooms (*Fomes fomentarius, Ganoderma applanatum, Ganoderma resinaceum, Inonotus obliquus, Schizophyllum commune, Trametes versicolor* and *Fomitopsis* species) are active against disparate families of viruses afflicting humans and bees is a strange, unexpected and nonobvious result to those skilled in the art of viral medicines fighting either flu or bee viruses. Such novel results are the subject of pending patent applications filed by the inventor, i.e. U.S. patent application Ser. No. 14/641,432: "Integrative fungal solutions for protecting bees," filed Mar. 8, 2015, and U.S. patent application Ser. No. 14/247,207: "Integrative fungal solutions for protecting bees and overcoming Colony Collapse Disorder (CCD): methods and compositions," filed Apr. 7, 2014.

An antiviral agent active against one virus does not mean, of course, that there will be antiviral activity against another. Indeed, compounds that have antiviral activity against all viruses are typically poisons, as viruses have specificity responses due to their unique modes of activity, infection, RNA and DNA compositions, transcriptomes and receptor fields on their membranes. Current thinking is there are more species of viruses on earth than all the species of fungi, plants and prokaryotes combined! And a universal antiviral is likely to kill off many beneficial viruses—a nascent subfield in virology. Hence, it is not obvious nor a medically justifiable theory that a hit against one virus means the same compound will be against all the species in the virome.

As viruses mutate and develop tolerances to antiviral medicines, the search for, discovery, and identification of new antiviral molecules is a priority for mitigating pandemics, whether natural or human-made. To this end, the inventor and his team have discovered that aqueous ethanolic extracts of the mycelia of polypore mushrooms native to the forests of the Pacific Northwest demonstrate remarkable activity in the standard assays for evaluating anti-flu, anti-herpes and anti-smallpox drugs. Particularly strong activity was noted against influenza viruses A and B.

Following the Project BioShield Act of 2004, Fungi Perfecti, LLC submitted over 200 hot water fruitbody and aqueous ethanolic extracts of the in vitro grown mycelia of mushroom species and strains within to the BioShield Bio-Defense Program administered by the U.S. Army Medical Research Institute of Infectious Diseases (USAMRIID) and the National Institutes of Health (NIH). Submitted samples were screened for antiviral activity coordinated through the Southern Research Institute (SRI). From the more than 200 samples the inventor provided to BioShield, 2,392 antiviral assays were performed on behalf of the inventor; 1,042 of which were influenza tests. From these 1,042 tests, 13 samples had $SI_{50}$>100, about a 1.2% success rate against any virus. Within a species such as Agarikon (*Fomitopsis officinalis*), an extract from one strain from this species, often showed significant antiviral activity against one flu virus, for instance, but not another. In essence, the probability of success proved highly unlikely and the negative results would be discouraging to other researchers bioprospecting large libraries of organisms for novel antivirals.

The protocols for determining antiviral activity are fully described by the National Institutes of Allergy and Infectious Diseases (NIAID) by Greenstone et al., NIAID resources for developing new therapies for severe viral infections, *Antiviral Res*., Volume 78, Issue 1, April 2008, Pages 51-59, hereby incorporated by reference in its entirety. The influenza bioassays were conducted according to Sidwell, R W and Smee, D F, In vitro and in vivo assay systems for study of influenza virus inhibitors, *Antiviral Res*., October 2000, 48(1):1-16., hereby incorporated by reference in its entirety.

Strong activity against orthopox viruses, influenza A, and influenza B was detected in *Fomitopsis officinalis* aka Agarikon, *Ganoderma resinaceum* (=*Ganoderma lucidum* var. *resinaceum*), aka Red Reishi, and *Inonotus obliquus*, aka Chaga, species of mushrooms which contain varying amounts of many of the active principle ingredients described herein, and moreover those specifically cited in the Claims.

As illustrated in Table 1, a percent solution of *Fomitopsis officinalis* extracts as low as 1-2% inhibited virus-induced cellular damage by 50% ($EC_{50}$) in the standard assays for screening antivirals. When the crude extract (100% solution) was diluted by a factor of $10^6$ (0.0001% solution), a 50% reduction in cellular damage by pathologically relevant influenza (influenza A and influenza B) and herpes viral (HSV) strains was observed. Selectivity Index (SI) numbers greater than 5 are moderately active, greater than 10 are highly active and greater than 100 are extraordinarily highly active.

TABLE 1

Antiviral Activity of ETOH/cold H2O extracts of mycelia of various compositions of mushroom species submitted to NIH contract labs under the "Bioshield" project. Influenza A and B (Flu A, B) assays were tested in MDCK cells against a Ribavirin control. Herpes Simplex (HSV) assays were tested in HFF cells against am Aciclovir control. Hepatitis C (HCV) assays were tested in Huh7 ET cells against an IFN alpha-2b control. The Selectivity Index (SI) scale is the ratio of cytotoxicity of the agent (CC aka IC) to the selective antiviral activity (EC) (EC50 for cell-based assays; IC50 for biochemical or subcellular assays) such that a SI >10 indicates extraordinarily strong activity.

| Cmpd Name | Virus | Strain | Assay | EC50 | EC90 | IC50 | SI | Cntrl EC50 | Cntrl EC90 | Cntrl IC50 | Cntrl SI |
|---|---|---|---|---|---|---|---|---|---|---|---|
| Flu A - Active Samples with SI >100 | | | | | | | | | | | |
| HDT3 1x | Flu A (H5N1) | Vietnam/1203/2004H | Visual | <0.0001 | | >0.1 | >1000 | 10 | | >320 | >32 |
| Fo-6 25x | Flu A (H3N2) | Wisconsin/67/2005 | Neutral Red | <0.0001 | | 0.026 | >260 | 2 | | >320 | >160 |
| EtOH only 24 hours | Flu A (H3N2) | Wisconsin/67/2005 | Visual | <0.0001 | | 0.032 | >320 | 1.9 | | >320 | >170 |
| Io-1 25x | Flu A (H5N1) | Vietnam/1203/2004H | Neutral Red | <0.0002 | | 0.04 | >200 | 12 | | >320 | >27 |
| 33 days | Flu A (H5N1) | Vietnam/1203/2004H | Visual | <0.001 | | 0.03 | >300 | 10 | | >320 | >32 |
| Host | Flu A (H5N1) | Vietnam/1203/2004H | Neutral Red | <0.0001 | | 0.02 | >200 | 12 | | >320 | >27 |
| Defense | Flu A (H5N1) | Vietnam/1203/2004H | Visual | <0.0001 | | 0.03 | >300 | 10 | | >320 | >32 |
| Gr 25x | Flu A (H5N1) | Vietnam/1203/2004H | Visual | 0.0002 | | 0.038 | 190 | 3.2 | | >320 | >100 |
| Io-1 25x | Flu A (H5N1) | Vietnam/1203/2004H | Visual | 0.0005 | | 0.057 | 110 | 3.2 | | >320 | >100 |
| Flu B - Active Samples with SI >100 | | | | | | | | | | | |
| Pb-1 25x | Flu B | Shanghai/361/02 | Neutral Red | <0.0001 | | 0.059 | >590 | 7.1 | | >320 | >45 |
| Gr 25x EtOH | Flu B | Shanghai/361/02 | Neutral Red | <0.0001 | | 0.04 | >400 | 7.1 | | >320 | >45 |
| only 24 hrs | Flu B | Shanghai/361/02 | Virus Yield | | 1E−04 | | 522 | | 37.72 | | >8.4 |
| Io-1 25x EtOH | Flu B | Shanghai/361/02 | Neutral Red | <0.0001 | | 0.035 | >350 | 7.1 | | >320 | >45 |
| only 24 hrs | Flu B | Shanghai/361/02 | Virus Yield | | 1E−04 | | 223 | | 37.72 | | >8.4 |
| Fo-13 25x EtOH | Flu B | Shanghai/361/02 | Visual | 0.0003 | | 0.047 | 150 | 1.7 | | >320 | >190 |
| only 24 hrs | Flu B | Shanghai/361/02 | Virus Yield | | 1E−04 | | 313 | | 37.72 | | >8.4 |
| | Flu B | Shanghai/361/02 | Visual-CONF | 0.0003 | | 0.047 | 150 | 1.7 | | >320 | >190 |

TABLE 1-continued

Antiviral Activity of ETOH/cold H2O extracts of mycelia of various compositions of mushroom species submitted to NIH contract labs under the "Bioshield" project. Influenza A and B (Flu A, B) assays were tested in MDCK cells against a Ribavirin control. Herpes Simplex (HSV) assays were tested in HFF cells against am Aciclovir control. Hepatitis C (HCV) assays were tested in Huh7 ET cells against an IFN alpha-2b control. The Selectivity Index (SI) scale is the ratio of cytotoxicity of the agent (CC aka IC) to the selective antiviral activity (EC) (EC50 for cell-based assays; IC50 for biochemical or subcellular assays) such that a SI >10 indicates extraordinarily strong activity.

| | | | | | | | | | | | |
|---|---|---|---|---|---|---|---|---|---|---|---|
| G. app 25x EtOH only 24 hrs | Flu B | Shanghai/361/02 | Visual | 0.0003 | | 0.057 | 180 | 1.7 | | >320 | >190 |
| | Flu B | Shanghai/361/02 | Visual-CONF | 0.0003 | | 0.057 | 180 | 1.7 | | >320 | >190 |
| Fo-10 25x EtOH only 24 hrs | Flu B | Shanghai/361/02 | Virus Yield | | 0.0001 | | 171 | | 37.72 | | >8.4 |
| Gr 25x | Flu B | Shanghai/361/02 | Neutral Red | 0.0004 | | 0.053 | 140 | 7.1 | | >320 | >45 |

HSV 1 - Active Samples with SI >100

| Cmpd Name | Virus | Assay | EC50 | EC90 | CC50 | SI | Cntrl EC50 |
|---|---|---|---|---|---|---|---|
| Fo-1 25x EtOH only 3 weeks | HSV-1 | CPE | 0.02 | >1 | 3.9 | 195 | 0.3 |

HCV - Active Samples with SI >10

| Cmpd Name | Virus | Assay | EC50 | EC90 | IC50 | SI 50 | Cntrl EC50 | Cntrl EC90 | Cntrl IC50 | Cntrl SI 50 |
|---|---|---|---|---|---|---|---|---|---|---|
| Tv EtOH only 24 hrs | HCV | HCV RNA replicon Confirmatory (Dose Response) | 5.59 | >100 | >100 | >17.9 | | | | |
| Positive Control IFN alpha-2b | HCV | HCV RNA replicon Confirmatory (Dose Response) | | | | | 0.07 | 0.38 | >2 | >28.6 |
| Positive Control IFN alpha-2b | HCV | HCV RNA replicon Confirmatory (Dose Response) | | | | | 0.12 | 0.54 | >2.0 | >16.7 |

Key:
Fo-1 = *Fomitopsis officinalis*, strain #1
Fo-6 = *Fomitopsis officinalis*, strain #6
Fo-10 = *Fomitopsis officinalis*, strain #10
Fo-13 = *Fomitopsis officinalis*, strain #13
G. app = *Ganoderma applanatum*
Gr = *Ganoderma resinaceum*
HDT3 = A blend of Fo-1, Gr, and Pb
Io-1 = *Inonotus obliquus*, strain#1
Pb-1 = *Piptoporus betulinus*, strain #1
Tv = *Trametes versicolor*
Host Defense = a 16 species blend, containing: *Fomitopsis officinalis*, *Ganoderma resinaceum*, *Piptoporus betulinus*, *Inonotus obliquus*, *Grifola frondosa*, *Cordyceps sinensis*, *Polyporus umbellatus*, *Agaricus brasiliensis*, *Phellinus linteus*, *Schizophyllum commune*, *Trametes versicolor*, *Hericium erinaceus*, *Ganoderma applanatum*, *Ganoderma oregonense*, *Fomes fomentarius*, *Lentinula edodes*

Fortunately, in 2014, the inventor's application to submit samples for continued antiviral testing was accepted by NIH Virology. However, NIH Virology refused to test extracts from mycelium due to their complexity but would, upon prior approval to submission, accept pure molecules, i.e. "structures" for testing. Pure compounds would only be tested if NIH Virology specialists vetted and approved the new structures as being ones not tested before by NIH, nor having evidence of activity against the viruses selected for study in the scientific literature, in order to eliminate redundancy. Since there can be more than 200,000 compounds resident in mycelia and mushrooms, the inventor was burdened with a seemingly impossible task: which compounds of more than 200,000+ molecules would be active against viruses? To conduct the bioguided fractionation tests standard in pharmaceutical discovery of new drugs typically would take years, as well as enormous laboratory resources.

The inventor, knowledgeable in the decomposition of wood by polypore mushrooms, and knowing that these polypore mushrooms contained polyphenols, focused on 20+ compounds related to polyphenols and related to acids produced in the de-lignification of wood, more specifically coumaric acids and their analogs and related congeners. NIH approved the first submission of 10 of 20 structures the inventor initially proposed for testing. Against tremendous odds, the first tests resulted in 3 of 10 structures being more active against a variety of viruses than the side-by-side positive drug controls used by NIH Virology testing laboratories. Upon the second submission, 5 of the 10 structures showed higher activity against viruses than cidofovir, the positive drug control, in tests against the human papilloma virus (HPV). In perspective, there are no good antivirals against HPV currently on the market, according to personal communication between the inventor and NIH Virology. Although an anti HPV vaccine has been developed, many will not receive it for a wide variety of medical and societal factors. Furthermore, millions of people are already infected with HPV who will not substantially benefit from vaccination (the recommended age for the vaccine is 11-12 years old, and not recommended after the age of 26). Having a novel antiviral that is active against HPV significantly serves public health by reducing the pathogen payload in the ambient infected population, reducing downstream communicability of disease, and in effect reducing deaths from cervical, anal, oral and other cancers.

Compounds were screened by NIH Virology contracted laboratories against a panel of viruses, resulting in significantly high activity against the human papilloma virus (HPV), varicella-zoster virus, norovirus (Norwalk), Epstein-Barr virus and polioviruses. To measure antiviral activity, the $SI_{50}$ was compared to a control drug for the same virus. The $SI_{50}$ is simply the $CC_{50}$, aka $IC_{50}$ (compound concentration that reduces cell viability by 50%) divided by the $EC_{50}$ (compound concentration that reduces viral replication by 50%). One sample (hispolon) showed modest activity against Ebola, a single-stranded RNA virus, with a $SI_{50}$>5.3, promising—as the $SI_{50}$ of the control drug, favipiravir, has only a $SI_{50}$>10. In a time of dire need for antivirals against Ebola, constituents related to hispolons merit further study with likelihood of discovering molecules closely related to hispolons that will be more antivirally active than favipiravir's $SI_{50}$>10. The inventor continues to pursue anti-Ebola compounds isolated from fungi.

A $SI_{90}$ in the Selectivity Index (SI) scale is the ratio of cytotoxicity of the agent vs. the selective antiviral activity ($CC_{50}/EC_{90}$) such that a $SI_{90}$>10 indicates extraordinarily strong activity whereby the compound concentration reduces viral replication by 90% and reduces cell viability by 50%.

Noteworthy is that very few antiviral medicines have significant $SI_{90}$'s >10. Acyclovir against varicella zoster is a good example to discuss. The $SI_{90}$ of acyclovir, ($SI_{90}$=6), is far less active as an antiviral than vanillic acid, claimed by this inventor, which has $SI_{90}$>195 against varicella zoster virus, a herpes virus causing "shingles." To achieve such high reduction of virus (90%) greatly underscores that vanillic acid and its analogs (for instance, p-hydroxybenzaldehyde and p-hydroxybenzoic acid) have high potential for becoming useful antivirals, especially since vanillin has a long history of safe use and is widely and safely consumed as a delicious edible flavoring. Vanillin is oxidized, after consumption, into vanillic acid.

Chrysin >98%, trans-cinnamic acid >98%, trans-ferulic acid >98%, quercetin hydrate >95%, rutin hydrate >98%, syringic acid >97% and vanillic acid >98% were obtained from TCI Chemicals. Hispolon 98% was obtained from Enzo Life Sciences. Ethyl 7-chloro-2-oxo-4-phenyl-2H-chromen-3-carboxylate, prepared according to Hwang et al., *J. Nat. Prod.* 76: 1916-1922 Supporting Information S-28-29 (2013), was obtained from the Department of Medicinal Chemistry and Pharmacognosy, College of Pharmacy, University of Illinois at Chicago, Chicago, Ill. 60612, courtesy of the authors. These compounds exhibited moderate to high antiviral activity according to the NIH Selectivity Index protocol in Table 2:

TABLE 2

Active Principal Ingredient (API) molecules with specific antiviral activity compared to the positive antiviral drug controls selected and tested by NIH Virology and their subcontractors.

| Chemical Name, ARB# | Chemical Structure | Activity |
|---|---|---|
| Ethyl-7-chloro-2-oxo-4-phenyl-2H-chromen-3-carboxylate ARB#14-000863 | 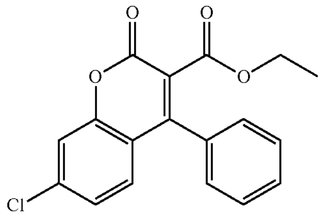 [SMILES: CCOC(=O)c1c(-c2ccccc2)c2ccc(Cl)cc2oc1=O] | Norovirus primary: SI50 = 25 (Control 2'C-methyl cytidine SI50 > 16) |
| Vanillic acid ARB#14-000866 | 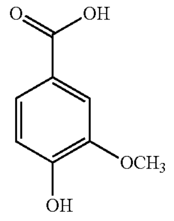 [SMILES: COc1cc(C(=O)O)ccc1O] | Varicella-Zoster primary: SI50 > 448 (Control acyclovir SI50 > 652), SI90 > 195 (Control acyclovir SI90 > 6) |
| Hispolon ARB#14-000869 | 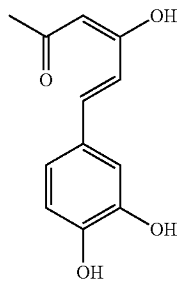 [SMILES: CC(=O)/C=C(O)\C=C\c1ccc(O)c(O)c1] | Norovirus primary: SI50 > 13 (Control 2'C-methyl cytidine SI50 > 16) Epstein-Barr primary: SI50 = 5 (Control cidofovir SI50 > 10) |
| Chrysin ARB#15-000498 | 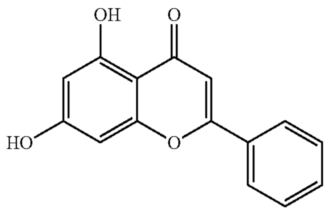 [SMILES: O=c1cc(-c2ccccc2)oc2cc(O)cc(O)c12] | Polio primary: SI50 > 15 (Control pirodavir SI50 > 22) |

TABLE 2-continued

Active Principal Ingredient (API) molecules with specific antiviral activity compared to the positive antiviral drug controls selected and tested by NIH Virology and their subcontractors.

| Chemical Name, ARB# | Chemical Structure | Activity |
|---|---|---|
| Quercetin hydrate ARB#15-000501 | 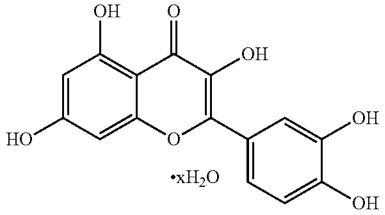 [SMILES: O=c1c(O)c(-c2ccc(O)c(O)c2)oc2cc(O)cc(O)c12] | Human papillomavirus 11 primary: SI50 > 60 (Control cidofovir SI50 > 12) |
| Rutin hydrate ARB#15-000502 | 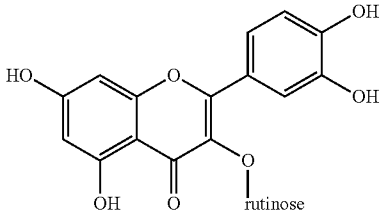 | Human papillomavirus 11 primary: SI50 > 109 (Control cidofovir SI50 = 12), SI90 = 5 (Control cidofovir SI90 = 1) |
| Syringic acid ARB#15-000503 | 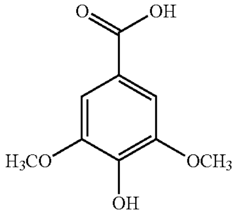 [SMILES: COc1cc(C(=O)O)cc(OC)c1O] | Human papillomavirus 11 primary: SI50 > 30 (Control cidofovir SI50 > 12) |
| trans-cinnamic acid ARB#15-00050 | 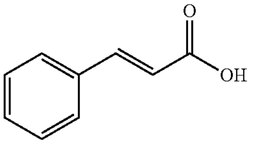 [SMILES: O=C(O)/C=C/c1ccccc1] | Human papillomavirus 11 primary: SI50 > 125(Control cidofovir SI50 > 12) |
| trans-ferulic acid ARB#15-000505 | 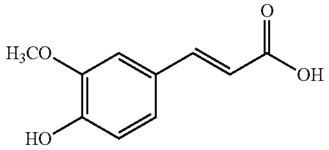 [SMILES: COc1cc(/C=C/C(=O)O)ccc1O] | Human papillomavirus 11 primary: SI50 > 125 (Control cidofovir SI50 > 12) |

Katayama et al. (2013) discloses that an enzymatically converted form of vanillic acid is antiviral.[13] This prior art by Katayama et al. (2013) does not make this inventor's discovery of vanillic acid being active against a herpes virus (varicella zoster) obvious for the following three reasons:

1) Noroviruses (tested by Katayama) are not related to herpes viruses (tested by the inventor). Norovirus (Norwalk virus) is in the Calciviridae and is a single stranded RNA virus and herpes viruses (varicella zoster, Epstein-Barr, etc.) are in Herpesviridae and are double stranded DNA viruses. These are about as distant as viruses can be. It is highly unlikely that an antiviral molecule would be active against such different viruses, and those skilled in the art of antiviral discovery would not assume activity against herpes viruses as an obvious logical extension of antiviral activity against noroviruses.

2) Vanillic acid in its pure form was not tested by Katayama, but rather novel enzymatically converted vanillic acid analogs synthesized by rutinases (rutinosylation).

3) This inventor's NIH tests of vanillic acid (Sample 14-00086) against the norovirus revealed a $SI_{50}$=1 and $SI_{90}$=1, meaning there is no activity of inhibition of vanillic acid against the norovirus. This provides strong evidence for the inventor's argument (1) above that activity against herpes viruses is not expected, anticipated, or an obvious extension of observed activity against noroviruses.

The inventor has taken on the lifelong task of comprehensively evaluating the antiviral activity of Agarikon (*Fomitopsis officinalis*), Amadou (*Fomes fomentarius*), Artist Conks (*Ganoderma applanatum, Ganoderma* annulare, *Ganoderma brownii*), Chaga (*Inonotus obliquus*), Red Reishi (*Ganoderma lucidum* sensu lato, *Ganoderma resinaceum, Ganoderma sinense, Ganoderma tsugae, Ganoderma oregonense*), the Split Gill Polypore (*Schizophyllum commune*), Turkey Tail (*Trametes versicolor*) and other polypores in the same clades and non-polypore mushrooms in the Agaricales. In pursuit of this goal, the inventor has surprisingly discovered that many of these same extracts of Agarikon (*Fomitopsis officinalis*), Chaga (*Inonotus obliquus*) and Red Reishi (*Ganoderma resinaceum, Ganoderma lucidum*), that reduce viruses afflicting human cells also significantly reduce viruses afflicting other animals, even honey bees (see U.S. patent application Ser. No. 14/641,432: "Integrative fungal solutions for protecting bees," 2015.). As such, this inventor believes these fungi are deep reservoirs of many novel antiviral molecules, offering a broad bioshield of defense against pathogenic viruses afflicting animals. Derivative of this discovery, the inventor predicts more antiviral molecules will be discovered, many of which are related to the herein described molecules listed in this patent application. The inventor predicts some of these molecules may also be active against viruses afflicting plants and hence useful for protecting agriculture.

These antiviral components are produced by many polypore fungi (polyporales) such as but not limited to *Fomitopsis officinalis, Fomitopsis pinicola, Fomes fomentarius, Inonotus obliquus, Ganoderma applanatum, Ganoderma oregonense, Ganoderma resinaceum, Ganoderma sinense, Ganoderma tsugae, Irpex lacteus, Schizophyllum commune, Trametes versicolor* and gilled fungi (Agaricales) such as *Pleurotus ostreatus, Pleurotus pulmonarius, Pleurotus populinus, Stropharia rugoso-annulata, Stropharia semigloboides, Stropharia ambigua, Psilocybe allenii, Psilocybe azurescens, Psilocybe coprophila, Psilocybe cubensis, Psilocybe cyanescens, Clitocybe odora*, and *Lactarius fragilis*.

The inventor predicts more antiviral molecules will be found within the extracellular and intracellular metabolites related not only to polyphenols and fatty acids, but also with molecules, which in association with each other, increase antiviral activity. Examples include but are not limited to: amylase, amyloglucosidase, betulinic acid, caffeic acid, protocatechuic acid, trans-cinnamic acid, ferulic acid, gallic acid, ellagic acid, lanosterol, inotodiol, trametenolic acids, hispolons (hispidins), hispidin, hypholomine B, inoscavin A, davallialactone, phelligridin D, ergosterols, chrysin, cordycepin, trans-o-coumaric acid, trans-p-coumaric acid, ellagic acid dihydrate, ergosterol, linoleic acids, transferulic acid, gallic acid hydrate, hexanal, hispolon, 4-hydroxybenzoic acid, p-hydroxybenzaldehyde, 4-hydroxybenzaldehyde, p-hydroxybenzoic acid, quercetin hydrate, rutin hydrate, (including related flavonoid glycosides), shikimic acid, syringic acid, vanillic acid, vanillin, ethyl vanillin, isobutyl vanillin, metabolic precursors of vanillin and vanillic acid, metabolic products of vanillin and vanillic acid, acetovanillone, guaiacol, eugenol, sulphurenic acid, dehydrosulphurenic acid, eburicoic acid, trans-cinnamic acid, trans-ferulic acid, 6-chloro-4-phenyl-2H-chromen-2-one, ethyl 6-chloro-2-oxo-4-phenyl-2H-chromen-3-carboxylate, 7-chloro-4-phenyl-2H-chromen-2-one, ethyl 7-chloro-2-oxo-4-phenyl-2H-chromen-3-carboxylate (and other coumarins), psilocybin, psilocin and their conjugate and ionic pharmaceutical salts, congeners, isomers, structural and functional analogs and significantly similar substituted analogs including hydroxylated, acetylated, methoxylated, ethoxylated and halogenated compounds known to those of skill in the art which may prove useful in the practice of this invention, including activity against viruses and oncoviruses. This would include, by way of example, but not of limitation: influenza viruses (H1N1, H3N2, H5N1, H5N2, H5N3, H5N8, H5N9, H7N1, H7N2, H7N3, H7N4, H7N5, H7N6, H7N7, H7N8, and H7N9, H9N1, H9N2, H9N3, H9N4, H9N5, H9N6, H9N7, H9N8, and H9N9), Herpesviridae viruses, herpes simplex virus-1, herpes simplex virus-2, human cytomegalovirus, murine cytomegalovirus, varicella zoster virus, Epstein-Barr virus, human herpes virus-6, human herpes virus-8, respiratory and other viruses including SARS coronavirus, respiratory syncytial virus, Ebola virus, Nipah virus, measles virus, adenovirus-5 virus, norovirus, rabies virus, Arenaviridae, Tacaribe virus, Pichinde virus, poliovirus, Junin virus, Lassa fever virus, Bunyaviridae, Rift Valley fever virus, Punta Toro virus, La Crosse virus, Maporal virus, Flaviviridae, dengue virus, West Nile virus, yellow fever virus, Japanese encephalitis virus, Powassen virus, Togaviridae, Venezuelan equine encephalitis virus, eastern equine encephalitis virus, western equine encephalitis virus, chikungunya virus, Picornaviridae, poliovirus, enterovirus-71, enterovirus-68, coxsackievirus B3, Papovaviridae, BK virus, JC virus, papillomavirus, Poxviridae, vaccinia virus, cowpox virus, monkeypox virus, polyoma, and hepatic viruses, hepatitis A virus, hepatitis C virus and hepatitis B virus. The compounds are also anticipated to be useful with all animals, including humans, mammals, birds, bats, pigs and bees, and with viral diseases carried by ticks, fleas, flies, mosquitos and other insects and arthropods.

With any new drug, the expense of production and availability are two factors determining whether or not the drug can be commercialized. The active principle ingredients (API) discovered by the author can be purchased "off the shelf" from a variety of chemical supply companies. The following prices are for small test quantities. Buying these en masse would drastically reduce the costs associated with each API. Given a target dose of approximately 100-200 mg. per day, the costs of many of these new antiviral molecules, with the exception of hispolon, are extraordinarily inexpensive. If buying masses of these API to fuel a supply chain and meet market demands, given the economies of scale going from 100 mg. to >1000 kg. per purchase order, the costs for each should be reduced at least 10×, and probably more. The following prices are retail prices available for research purposes buying 100 mg. ($1/10^{th}$ of a gram) before negotiation for discounts.

Chrysin: TCI Chemicals, >98%, $0.39/100 mg trans-Cinnamic acid: TCI Chemicals, >98%, $0.038/100 mg trans-Ferulic acid: TCI Chemicals, >98%, $0.15/100 mg Hispolon: Enzo Life Sciences, ≥98%, $1280.00/100 mg Quercetin hydrate: TCI Chemicals, >95%, $0.15/100 mg Rutin hydrate: TCI Chemicals, >98%, $0.12/100 mg Syringic acid: TCI Chemicals, >97%, $0.16/100 mg Vanillic acid: TCI Chemicals, >98%, $0.12/100 mg Cidofovir, an injectable antiviral against which many of these molecules (APIs) were favorably compared is very expensive and the generic form currently sells for $342 to $626 for 5 doses in per vial (5 ml) containing 75 mg/ml (generic). The least expensive comparative antiviral is acyclovir (now off patent) and sells for $7.59 for 200 mg. By way of example, the inventor's APIs against Human Papilloma Virus (HPV), showed high antiviral activity using molecules many orders of magnitude less expensive than cidofovir.

While focusing on the delignification and cellulose-decomposing pathways and byproducts from mushroom mycelium of species from the Polyporales and Agaricales, and studying how to save bees from colony collapse disorder, the inventor observed high attractancy of the extracellular droplets exuding from the mycelium mushrooms, initially of a gilled mushroom in the Agaricales (*Stropharia rugoso-annulata*), when a patch of mycelium of this species was planted in his garden. When the mycelium grows on wood or grains, it decomposes lignin-cellulosic, hemi-cellulosic or cellulosic components and expresses polyphenol-like compounds. Focusing on p-coumaric acid, the inventor scoured the scientific literature, which showed that coumaric acid was essential for activating the gene sequences for the cytochrome p450 detoxification pathways in bees. Constellations of molecules were then explored by the inventor for antiviral activity and, surprisingly, many of these acids showed the strong antiviral activity, as noted within this patent application.

Consideration of metabolic pathways supposedly unrelated to antivirals provided inspiration and guidance in selecting many of the currently disclosed compounds for testing. For example, Terrón et al., Structural close-related aromatic compounds have different effects on laccase activity and on Icc gene expression in the ligninolytic fungus *Trametes* sp. 1-62*, Fungal Genet. Biol.,* 41:954-962 (2004) teaches: "Nine phenolic compounds (p-coumaric acid, ferulic acid, guaiacol, syringol, p-methoxyphenol, pyrocatechol, phloroglucinol, 3,5-dihydroxybenzoic acid, and syringaldazine) were tested for their ability to increase laccase production in the ligninolytic basidiomycete *Trametes* sp. 1-62. All these compounds resulted in increases in laccase activity, with the highest levels being detected in the presence of p-coumaric acid (273-fold) and guaiacol (73-fold)." The inventor, while researching what compounds activate the cytochrome P450 detoxification pathways in bees, and how *Trametes versicolor* mycelium uses enzymes for delignifying lignin (in wood) and cellulose (in paper, grains, starch), found the co-occurring molecules particularly surrounding p-coumaric acid to be interesting to test for antiviral activity. Although the inventor's curiosity in his pursuit of helping bees to overcome colony collapse disorder led him to look at coumaric acid, and this spurred him to send to NIH Virology an assortment of molecules related to coumaric acid, it is interesting to note that, to date, coumaric acid has not demonstrated any antiviral activity. The inventor will continue to look at coumaric acids and their congeners as a source of novel antivirals. Nevertheless, this further speaks that the inventor's discovery being unobvious and indeed bizarre.

With the active principal ingredients put forth by the inventor herein, compounds new to science with these multifaceted properties are first described. All compounds and mixtures containing these compounds can be administered using any method known to the art of pharmaceutical drug delivery, including new nanotechnologies and microbiome therapies allowing for controlled release, enhancement and targeting of medicines.

These active principle ingredients (APIs) can be found in both fungi and plants, and can be combined with each other, or with other drugs, or attached to other molecules to increase their pharmacokinetic effectiveness, specificity, and/or longevity of effects in order to confer a medical benefit. Additionally, The APIs can be embedded within carrier molecules of greater complexity, which upon digestion, allow for the APIs to pass into the blood stream in an amount effective to be impart an antiviral and immune supporting benefit.

More novel antiviral molecules are expected to be discovered, derivative of this invention, from Amadou (*Fomes fomentarius*), Agarikon (*Fomitopsis officinalis*), Red Belted Polypore (*Fomitopsis* pinicola), Artist Conk (*Ganoderma applanatum*), Red Reishi (*Ganoderma lucidum* or *Ganoderma resinaceum*), *Ganoderma sinense*, Chaga (*Inonotus obliquus*), Mesima (*Phellinus linteus*), Split Gill Polypore (*Schizophyllum commune*), Turkey Tail (*Trametes versicolor*) and their closely related species within the same taxonomic Glade or clades from which these species evolved, using the methods known to the art of pharmaceutical drug discovery. Compounds discovered by the inventor existing in non-mushroom forming fungi and in bacteria and plants may also impart antiviral activity to other viruses not yet tested. Moreover, combinations of these active principle ingredients and their congeners are expected to also reduce viruses such as hepatitis, flu, SARS (severe acute respiratory syndrome), MERS (Middle Eastern respiratory syndrome), and other viruses, some yet not known to science. This discovery offers an umbrella of protection, an armamentarium, a broad bioshield or "mycoshield" of defense against one or a plurality of viruses causing disease.

Example 1

Although ethanol and water extracts are illustrated within this invention, it will be obvious that the various solvents and extraction methods known to the art may be utilized.

The extracts may optionally be prepared by methods including extraction with water, alcohols, organic solvents and supercritical and subcritical fluids such as $CO_2$, and from extracts derived from fermentation with bacteria such as but not limited to *Bacillus subtilis*. Extracts may also be prepared via steam distillation of volatile components, similar to the preparation of "essential oils" from flowers and herbs. Suitable alcohols include those containing from 1 to 10 carbon atoms, such as, for example, methanol, ethanol, isopropanol, n-propanol, n-butanol, 2-butanol, 2-methyl-1-propanol (t-butanol), ethylene glycol, glycerol, etc. Suitable organic solvents include unsubstituted organic solvents containing from 1 to 16 carbon atoms such as alkanes containing from 1 to 16 carbon atoms, alkenes containing from 2 to 16 carbon atoms, alkynes containing from 2 to 16 carbon atoms and aromatic compounds containing from 5 to 14 carbon atoms, for example, benzene, cyclohexane, cyclopentane, methylcyclohexane, pentanes, hexanes, heptanes, 2,2,4-trimethylpentane, toluene, xylenes, etc., ketones containing from 3 to 13 carbon atoms such as, for example, acetone, 2-butanone, 3-pentanone, 4-methyl-2-pentanone, etc., ethers containing from 2 to 15 carbon atoms such as t-butyl methyl ether, 1,4-dioxane, diethyl ether, tetrahydrofuran, etc., esters containing from 2 to 18 carbon atoms such as, for example, methyl formate, ethyl acetate, butyl acetate, etc., nitriles containing from 2 to 12 carbon atoms such as, for example acetonitrile, proprionitrile, benzonitrile, etc., amides containing from 1 to 15 carbon atoms such as, for example, formamide, N,N-dimethylformamide, N,N-dimethylacetamide, etc., amines and nitrogen-containing heterocycles containing from 1 to 10 carbon atoms such as pyrrolidine, 1-methyl-2-pyrrolidinone, pyridine, etc., halogen substituted organic solvents containing from 1 to 14 carbon atoms such as, for example, bromotrichloromethane, carbon tetrachloride, chlorobenzene, chloroform, 1,2-dichloroethane, dichloromethane, 1-chlorobutane, trichloroethylene, tetrachloroethylene, 1,2-dichlorobenzene, 1,2,4-trichlorobenzene, 1,1,2-trichlorotrifluoroethane, etc., alkoxy, aryloxy, cyloalkyl, aryl, alkaryl and aralkyl substituted organic solvents containing from 3 to 13 carbon atoms such as, for example, 2-butoxyethanol, 2-ethoxyethanol, ethylene glycol dimethyl ether, 2-methoxyethanol, 2-methoxyethyl ether, 2-ethoxyethyl ether, etc., acids containing from 1 to 10 carbon atoms such as formic acid, acetic acid, trifluroacetic acid, etc., carbon disulfide, dimethyl sulfoxide (DMSO), nitromethane and combinations thereof. Extracts may also be prepared via sequential extraction with any combination of the above solvents or methods mentioned herein. The extracts may be further refined by means known to the art to a more potent antiviral form or an active pharmaceutical ingredient.

Preferred drying methods include freeze drying, air drying, infrared drying, spray drying, vacuum drying, membrane drying, sonification drying, vibrational drying, drum drying, light drying and Refractance Window® drying methods and apparati for drying mycelium, extracellular metabolites, natural product extracts and derivatives as disclosed in U.S. Pat. No. 4,631,837 to Magoon (1986), herein incorporated by reference in its entirety. Extracts are preferably extracted from living or frozen mycelium and may be cell-free (filtered and/or centrifuged) or not.

Example 2

At the end of May 2015, the inventor supplied 50 kg of freeze-dried mycelium of Agarikon (*Fomitopsis officinalis*) to a free-range chicken farm of 20,000 chickens, in the center of the bird flu pandemic that ravaged Iowa and Minnesota (this was a test, and provided by the inventor at no charge). The avian influenza strain H5N8 contributed to H5N2 variants to create a new strain of highly communicable and lethal avian influenza. The chickens were fed at a rate of 0.25 gram per day per chicken of Agarikon mycelium—freeze dried and heat sterilized on a rice substrate, made according to the specifications listed in this and the aforementioned patent applications by the inventor, and was applied with their normal feed at a rate of 1.9 lbs/ton.

The chickens not treated, in the surrounding area, tested positive for avian influenza and had to be subsequently euthanized. The chickens fed with Agarikon mycelium survived with no trace of bird flu. An island of immunity in the midst of a pandemic was observed with the Agarikon-treated chickens. The owners of the chicken farm, who are major stakeholders in the chicken industry, were sufficiently impressed to engage the inventor for supplying chickens with Agarikon mycelium to prophylactically treat chickens prior to the next bird flu outbreak. Agarikon mycelium contains many of the antiviral compounds described herein. Containing a complexity of antiviral molecules, the inventor sees Agarikon and the other fungi, especially polypores listed herein, offering a broad bioshield of protection from pathogenic viruses by offering an extract or specialized dried form of mycelium as a feed supplement. The potential market for protecting the chicken and turkey industry is in the hundreds of millions of dollars. Given these initial tests, approximately 1,000 kg of mycelium (a metric ton) is equivalent to 40,000,000 chicken-days of protection (after three weeks of non-detection of the flu virus, the chickens are considered 'bird virus free' and are allowed to be sold for consumption). The Agarikon mycelium can be marketed and sold as a nutraceutical or as a pharmaceutical food standardized to identifiable markers for batch-to-batch consistency.

Example 3

In tests initiated and by cause of the inventor, the following antiviral activity was reported by NIH contracted virologists. These results show antiviral activity of high significance and potential utility for creating new drugs and new compositions of drugs, treatments, prophylactics, adjuvants, nutraceuticals, animal feeds and dietary supplements. By way of example and not of limitation, these compositions may include pure compounds, nearly pure isolates or fractions, extracts of natural products containing the disclosed molecules and synthesized molecules identical to the naturally occurring molecules, herein described and claimed as novel antiviral agents of significance against multiple viruses.

Pure or nearly pure molecules were submitted by the inventor via his solely owned business Fungi Perfecti, LLC, and his employee Dr. Regan Nally, to Dr. Mark Prichard, University of Alabama (UAB) Birmingham, Ala. 35233 to test for anti-human papillomavirus (HPV) activity via NIH Virology, using protocols conforming to standards established by the National Institutes of Health/Virology. Dr. Mark Prichard's team analyzed the inventor's molecules against HPV (human papillomavirus) using state-of-the-art testing methods utilizing quantitative polymerase chain reaction (DNA)/CellTiter-Glo (Toxicity) protocols.

In general, extracts of those species and strains of mushrooms, or purified molecules occurring within them, or synthetic versions of such molecules, or analogs of such molecules, that are active against viruses with a $SI_{50} \geq 5$ are preferred, with $SI_{50}>10$ being more preferred and $SI_{50}>30$ being most preferred. Any compound having $SI_{50}>100$ is considered extremely active and extraordinarily selective.

The primary screening of vanillic acid against varicella zoster (the "shingles" or human herpesvirus 3, HHV-3) virus resulted in high activity with an $SI_{50}>448$ and $SI_{90}>195$ compared to the positive drug control acyclovir which, in the same, side by side test, had a $SI_{50}>26$ and a $SI_{90}>1$.

This compound, vanillic acid, is produced as a by-product in the delignification of wood by *Fomitopsis, Ganoderma, Inonotus* and other fungi, particularly the wood decomposers. Vanillic acid is also produced through metabolic oxidation of vanillin, the common flavoring, upon ingestion. Vanillin can be synthesized or sourced from a wide variety of plants—even from manure! Vanillin is readily available in quantity, making it a uniquely favorable and flavor-able prime candidate for further testing and rapid commercialization, as this is a well-known and safe food ingredient. The amount of vanillic acid, the oxidized form of vanillin, and the correlated dosages for an antiviral based on side-by-side comparisons of vanillic acid to acyclovir, falls well within a safe amount for a 70 kg human, i.e. 700 mg vanillin per day or for a 88 kg American male, 880 mg vanillin per day. The average concentration of vanillin in the vanilla flavoring available to consumers ranges from 0.38 to 8.59 mg/ml. Hence, for a person to gain antiviral benefit from drinking vanilla extract would mean ingesting unrealistic volumes of vanilla extract and at a very high expense.

Vanillin and vanillic acid are common molecules in the plant world, notably *Angelic sinensis* or Dong Quai has some of the highest amounts of vanillic acid found in nature. "The majority of industrially produced vanillin is ingested in the form of food and beverages. Minor amounts are applied topically as skin care products, perfumes, etc. The global use of vanillin in food and beverages imply that almost every human globally is exposed to minute amounts of vanillin by ingestion, although individual doses and exposure can vary due to eating habits and preferences. An Acceptable Daily Intake (ADI) of 10 mg/kg has been agreed between FAO/WHO and EU. For a 70 kg person the ADI is 700 mg vanillin which, as an example, corresponds to minimum of 700 g chocolate, or 7,000 g of ice cream. For the risk assessment it is assumed that even persons with a high intake of vanillin containing food and beverages do not have a vanillin intake above the ADI."[14]

However, 700-880 mg of vanillin is within the therapeutic dosage window to impart antiviral effects for a 70-88 kg person. For the average American male, buying an effective dosage of 880 mg. of vanilla from a grocery store is an impractical amount for consumers to ingest using the concentrated vanilla flavorings which are commonly available.

More information can be found in the Handbook of Vanilla Science and Technology (2011), edited by Dahna Havkin-Frenkel and Faith Belanger.

Although naturally occurring, the use of vanillic acid and vanillin as antivirals is novel. Note that vanillin has many analogs and closely related compounds, some of which are described herein as being antiviral and more of which are expected to be antiviral.

There is an emergent need for new antivirals active against varicella zoster and other herpes viruses due to emerging drug resistance as these strains mutate. Vanillic acid, and its closely related acids, offer new sources for antiviral medicines that are inexpensive to make. At a time of crisis when few new safe antiviral drugs are coming onto the market, vanillic acid can be easily manufactured, standardized for potency and studied clinically with little expectation of harm compared to most new antivirals. Moreover, vanillic acid has good pharmacokinetics. Vanillic acid from oral ingestion remains in the blood stream post-digestion for more than 11 hours—a pharmacokinetic advantage because this compound will have prolonged cell-viral contact, which strengthens its potential as an advantageous antiviral drug.

Since up to 95% of vanillin is metabolized within the human body into vanillic acid, vanillin and its enzymatically converted analogs, are also predicted to be primary antiviral agents against viruses, particularly against herpes viruses related to varicella zoster viruses. Varicella zoster is one of nine currently known herpes viruses infecting humans, at least three of which are thought to be oncoviruses: herpes virus 4 (HHV-4=Epstein-Barr); herpes 6 (HHV-6); and herpes 8 (HHV-8)). HHV-6 has been detected in lymphomas, leukemia, cervical cancers, Karposi sarcoma and brain tumors. Herpes viruses are also neurotoxic and often are associated, with or without causality, to the neurodegeneration and neuropathic inflammation often associated with the Alzheimer's disease complex. Moreover, vanillic acid and the other compounds, compositions, and derivatives disclosed herein can upregulate cytochrome enzymatic pathways, specifically in genes coding for cytochrome p450, and the p21 and p53 pathways for up-regulation and production of tumor necrosis proteins. Hence having more than one benefit from these aforementioned APIs can synergistically result in compounded benefits useful to medicine. For medicines to have antiviral, antibacterial, immune enhancing, antioxidant, and tumor de-cloaking properties with P21 and P53 gene activation effects, post ingestion, represent a novel anticancer armamentarium of active agents. The more synergistic benefits we have available for our cells to combat disease, the more likely a positive outcome. Rather than finding a single agent against a single virus, presenting an animal with a menu of benefits provides a broader shield of protection.

Example 4

The NIH virology report on the inventor's compounds tested against HPV noted that five samples are "highly active," being designated in red lettering by NIH virology for emphasis. Table 2 (listed previously) shows that 5 of the 10 molecules submitted in one set demonstrated significant antiviral HPV activity, with Selectivity Indexes (SI)>10. Other isoforms related to these compounds are expected to confer even greater antiviral activity and complementary benefits, beyond antiviral activity, making them more useful in medicine for treating diseases.

The primary screening of potential antiviral molecules against the human papillomavirus (HPV) were compared against cidofovir, the positive drug control, which showed a $SI_{50}>12$; $SI_{90}=1$. The Selectivity Indexes for testing of the inventor's selected molecules against HPV are as follows: quercetin hydrate $SI_{50}>60$; rutin hydrate $SI_{50}\geq 109$; syringic acid $SI_{50}>30$, trans-cinnamic acid $SI_{50}>125$ and trans-ferulic acid $SI_{50}>125$.

In general, those species and strains of mushrooms, or purified molecules occurring within them, or analogs of those molecules, that are active against HPV having a $SI_{50}\geq 5$ are preferred, with $SI_{50}>10$ being more preferred and $SI_{50}>30$ being most preferred. Any compound having $SI_{50}>100$ is considered extremely active and extraordinarily selective against HPV, with low toxicity to human cells, and thus has high clinical potential for the prevention of HPV cross infection. Of note is that there are very few antiviral drugs active against HPV, and vaccinations are partially effective, yet controversial, with long term consequences still to be determined. All the above five mentioned molecules selected and submitted on behalf of the inventor greatly exceeded cidofovir's anti-HPV activity.

Example 5

Hispolon (ARB#14-000869) also showed, according to NIH Virology, 'moderately active' antiviral activity against the Epstein-Barr oncovirus with a $SI_{50}=5$ compared to the positive drug control cidofovir which has a $SI_{50}>10$.

Example 6

Poliovirus infections continue to spread around the world. Although smallpox is thought to be successfully eradicated, polio still survives despite widespread vaccinations. Few effective antiviral drugs have been discovered. Virology tests at Utah State University (USU) Institute for Antiviral Research at Logan, Utah, under contract to NIH Virology, screened numerous antiviral candidates submitted by the applicant. One molecule in particular, chrysin, demonstrated moderate to high levels of antiviral activity inhibiting the polio virus with a $SI_{50}>15$ compared to the positive drug control, pirodavir, which had a $SI_{50}=22$. Hence, chrysin and its derivatives and analogs may prove to be new antivirals to help reduce the poliovirus.

Example 7

Very few compounds have shown dual activity against viruses and bacteria. Ethyl 7-chloro-2-oxo-4-phenyl-2H-chromen-3-carboxylate (a synthetic analog of the naturally occurring 6-chloro-4-phenyl-2H-chromen-2-one and ethyl 6-chloro-2-oxo-4-phenyl-2H-chromen-3-carboxylate) and hispolon are two such compounds, not only active against the norovirus (ethyl-7-chloro-2-oxo-4-phenyl-2H-chromen-3-carboxylate $SI_{50}=25$ and hispolon $SI_{50}>13$) but also against the bacterium *Mycobacterium tuberculosis* as co-discovered by this applicant who is a co-author of "Chlorinated coumarins from the polypore mushroom *Fomitopsis officinalis* and their activity against *Mycobacterium tuberculosis*," Hwang et al., *J. Nat. Prod.* 76: 1916-1922 (2013).

Such dual antiviral and antibacterial activity against the tuberculosis causing bacterium, *Mycobacterium tuberculosis*, and the Norwalk virus (norovirus), a virus notoriously problematic on cruise ships, makes these unique medicines useful for protecting people traveling in close quarters from viral and bacterial infections and useful for protecting and benefitting public and environmental health and reducing the impacts of diseases in animals, particularly humans.

The rapid spread of the norovirus and the high infectivity trends with multi-drug resistant tuberculosis are but one example of a complex disease state wherein people's health is threatened by more than one contagion. As such, ethyl 7-chloro-2-oxo-4-phenyl-2H-chromen-3-carboxylate and hispolon, and compositions containing these compounds, can protect passengers, patients, travelers or people wherever they congregate from multiple assaults from viral and bacterial infections. Congeners and analogs of ethyl 7-chloro-2-oxo-4-phenyl-2H-chromen-3-carboxylate and hispolon are expected to show improved efficacy against viral and bacterial infections. Delivery systems include but are not limited to sprays, capsules, tablets, elixirs, emulsions, lozenges, suspensions, syrups, pills, lotions, epidermal patches, suppositories, inhalers and injectables, or by other means known to the art of drug delivery. For measured, long term dosing and to achieve a more consistent effect, delayed release delivery systems can be employed.

In medicine, conventional thinking is that drugs cannot be dually antiviral and antibacterial. Hence, these compounds, and others related to them, are likely to impart a broader shield of protection from infection caused by pathogenic, infectious viruses and bacteria. These compounds may be the first among many showing dual activity against these two disparate categories of infectious agents. Since the average person is blind to knowing whether an infection is from a virus or a bacterium, and since bacterial infections are notoriously common (and often deadly) subsequent to a viral infection, this invention serves an important function in broadly protecting public health—before infection, at the time of infection or post infection. This discovery may lead, derivatively, to a whole new class of medically useful agents, methods, compositions and treatments.

Example 8

A 58-year old male was diagnosed with an unusual (cytokeratin 7 positive) Merkel cell carcinoma (MCC). After various procedures and completion of radiation therapy, a positron emission tomography (PET) scan showed no evidence of disease. During a regular follow-up six months after completion of radiation therapy, a PET scan revealed a liver lesion, confirmed by magnetic resonance imaging (MRI). Histological features were consistent with his primary MCC tumor. Surgery and radiation were not possible given the location of the tumor; the patient refused chemotherapy because of the relatively poor outcomes and significant side effects associated with chemotherapy treatment of MCC. The patient began taking dietary supplements, liver and colon cleanser and Stamets 7®, a blend of medicinal mushroom mycelium [Royal Sun *Blazei* (*Agaricus brasiliensis* f. *blazei*), *Cordyceps* (*Cordyceps sinensis* s.l.), Reishi (*Ganoderma lucidum* s.l.), Maitake (*Grifola frondosa*), Lion's Mane (*Hericium erinaceus*), Chaga (*Inonotus obliquus*) and Mesima (*Phellinus linteus*)] and markedly altered his diet by removing meat, eggs and dairy and substituting organic brown rice, beans, sautéed vegetables and freshly prepared juices of organic vegetables. Five weeks after beginning these alternative approaches, a MRI revealed complete remission of his liver metastasis, and he has remained asymptomatic for a total of 53 months, with the most recent scan showing no evidence of disease. See Vandeven et al., Complete Spontaneous Regress of Merkel Cell Carcinoma Metastatic to the Liver: Did Lifestyle Modifications and Dietary Supplements Play a Role?, *Glob. Adv. Health Med.,* 1(5): 20-21 (2012). Antiviral components within the Stamets 7® formulation may be responsible for the reduction of MCC and may have helped this patient recover from the ensuing cancer.

Example 9

A complex mixture of mycelium of 17 medicinal mushroom species in a product called MyCommunity® and a 7 species blend called Stamets 7® under the Host Defense® brand of Fungi Perfecti (P.O. BOX 7634, Olympia, Wash. 98507) has been attributed by several customers to alleviate Lyme disease symptoms. Within this mixture, Lion's Mane, *Hericium erinaceus*, and *Cordyceps subsessilis*, have been anecdotally reported by Lyme disease victims to result in relief of symptoms. Lyme disease is caused by *Borrelia* species, particularly the *Borrelia burgdorferi* bacterium, and cohorts, which can co-infect, causing inflammation and lowering immunity, making patients more susceptible to latent or opportunistic infections and carcinogenesis. The species and compounds mentioned herein, therefore, hold promise in new methods and compositions for drug and nutraceutical uses for treating patients suffering from Lyme disease and the related pathologies, symptomologies, and co-infections seen with people with this debilitating, chronic illness. Antibacterial components within the Stamets 7® and MyCommunity® formulations may be responsible for the reduction of Lyme disease and may help relieve symptoms.

Example 10

A physician reported that his hepatitis C viral counts became undetectable after taking a two month regimen of Agarikon Host Defense® capsules containing *Fomitopsis officinalis* mycelium grown on rice (500 mg per capsule). Reprinted, with permission is an exact copy of his case report.

"Here are the facts of my case.

I was diagnosed with hepatitis C in 2000 or 2001. An abnormal liver panel had alerted the MD to check for that virus, as that's about the time that medicine was realizing its spread.

How I got the virus I've never figured out, but I had worked on an inpatient psychiatric unit in SoCal in 1987/88. After that I managed large outpatient mental health clinics down there where a significant number of our patients had this virus. Another possibility is that I got it from a major surgery I had in 1992. In any case, the MD in 2001 said that since my viral load was low, I should wait until better treatments were available before seeking care.

As you probably know, excellent treatments recently became available (though expensive). My internist agreed this January to check my viral load again and although it was still relatively low, he agreed to refer me to a gastroenterologist anyway. That fellow did a liver panel and then at my pleading referred me on to the pharmacist for the course of medication. That's how Kaiser Permanente® does it—a specially-trained pharmacist manages a treatment program. It starts with a baseline check of the viral load, then the daily medication. As soon as the viral load drops to zero, the medications are stopped.

The week before I was to attend the class, the pharmacist ordered another HCV lab test to establish the baseline. On the day of the class, I was literally in the facility, walking to the classroom when the pharmacist called my cell phone. She said the lab test results had just come in and somehow, for some reason, it showed no virus present. She was stumped for an explanation, but said that I couldn't start the medication because I had no viral load to try to reduce.

I called the gastro back next day and said maybe there had been a lab error or something. It had been so hard to get the referral I didn't want to lose this chance to get rid of the virus. He agreed to have the test redone right away, just in case. A week later he called to say that sure enough, the first test was correct. There was no viral load—I'm apparently virus free. He seemed uncertain but said he's heard stories of patients whose immune system was able to clear the virus somehow, but he had never heard of anyone who had carried a viral load for more than 10 years and then have it just disappear like this. He said he had reviewed my records and the viral load had been consistent between first identification and the most recent test in January 2015. But it was gone now, seven months later. And the load was still zero on re-test two weeks later. He said I should be happy.

And it is indeed a relief, as you can imagine. I thought hard for an explanation. It dawned on me that during the spring of this year, I'd taken the Agarikon capsules for maybe two months. Other than that, I was taking curcumin and a vitamin, but had been taking those for years. The only change was adding the mushroom capsule.

I'd heard an interview with you on the radio. (I don't recall what show, but it was in the middle of the night when I couldn't sleep). You didn't say anything about HCV but you had mentioned the antiviral effect of certain mushrooms. I did a literature search and came across an article or patent of yours (I forget which) in which HCV was specifically mentioned, which is why I ordered the Agarikon from your company.

So that's my story. Obviously it's not a lab-controlled experiment, but I've thought hard about other possible explanations and don't have many. I hadn't changed any other lifestyle or dietary habit. So either this remission is due to (a) meditation and prayer, (b) random good fortune, (c) the Agarikon, or (d) some combination of those.

I used two 60-capsule bottles of Agarikon between April and June. I always took one capsule in the morning before breakfast, and sometimes a second capsule in the evening before sleep, but that wasn't consistent. We were down in SoCal in June and July and I wasn't taking the capsules there, but the lab tests that came back negative were done in August (done at the Kaiser facility in Fontana, Calif.). So any beneficial effect must have been in the spring Feel free to share my story as appropriate, but I'd prefer to stay anonymous of course."

Example 11

Numerous analogs of hispolons, including hispidin, may be useful as antiviral and antibacterial medicines. At least 26 related analogs are known thus far, and the inventor sees these as being prime candidates for new treatments against viruses, oncoviruses and pathogenic bacteria, and as anti-inflammatories. As such, hispolons offer a unique synergy of benefits for protecting animal health via multiple pathways. Some, but not all of these can be found in Balaji et al., Design, Synthesis and In Vitro Cell-based Evaluation of the Anti-cancer Activities of Hispolon Analogs, *Bioorganic & Medicinal Chemistry* 23: 2148-2158 (2015).

These compounds may directly, or indirectly, positively influence disease outcomes, as they work via separate pathways and activate sets of receptors, which cumulatively and synergistically enhance immunity, overcome toxicity of xenobiotic toxins, have antiviral and antibacterial properties and potentiate benefits from other drug therapies.

Example 12

Any of the antiviral molecules and their analogs described within this invention can be combined with CBD (cannabidiol) to provide a dual, synergistic benefit for reducing oncoviruses and up-regulation of immune system pathways, resulting in the cumulative benefit of reducing viral burdens and reducing carcinogenesis. Moreover, the natural products such as mushrooms, fungal mycelium and extracts of fungal mycelium containing the antiviral molecules described herein can be combined with CBD in its purified forms, or with other cannabinoids, or with its natural forms, such as with *Cannabis* species, or extracts thereof, for medical benefit. Additionally, foods can be designed with natural substances containing these aforementioned compositions and antiviral pharmaceutical agents, with and without CBD, specifically to appeal to consumers for maintaining health and preventing and curing diseases. There are at least 85 cannabinoids currently known, any one or combination of which can be utilized for creating a composition of ingredients for medical benefit. Moreover, these ingredients can be combined without making medical claims and conforming to the Dietary Supplement Health and Education Act (DSHEA) of 1994, such as but not limited to supportive statements such as: in support of immunity, in support of innate health states in healthy individuals, in support of a healthy microbiome, and in support of healthy genetic expression. Hispolons, polyphenols, mycoflavonoids, and the antiviral acids shown herein are prime candidates for combining with CBDs to create novel component mixtures. The rationale for combining CBDs and fungal immune enhancing and antiviral constituents is that both CBDs and fungal polysaccharides act to potentiate the immune system. Their mechanisms of action are complementary; respective receptor sites are able to cascade reactions that are similar to and that are different from one another, allowing the interplay of these agonists to tune the immune system according to one's state of health.

CBD from *Cannabis* significantly complements the immune modulating capacities of fungal polysaccharides. Fungal polysaccharides (fungal PS) are agonists for a few key pattern recognition receptors such as TLRs 2, 4, 6 and Dectin-1. These receptors are expressed on immune cells that regulate cell-mediated immunity, such as macrophages, NK cells, and others. Activation of these cells initiates cross-talk with the complement system and, current research suggests, humoral branches of the immune system. Agonist activity at these receptor sites activates MAPK and MyD88 pathways, activating Nf-kappaB. Fungal PS also activate Th1 cells, which coordinate the cell mediated immune response.

CBD is a weak agonist (with low affinity) at the CB2 receptor site, which is expressed on all immune cells and tissues (i.e. tonsils, spleen). The pharmacology of CBD is still being investigated. From what is currently known, CBD downregulates TNF-alpha. This is of interest, as TNF-alpha can be upregulated by fungal PS. CBD is also a weak agonist at GPR55, also known in some circles as the CB3 receptor. This receptor is expressed on a diverse array of cells in the body, and is increasingly being researched for its role in endocannabinoid homeostasis (appetite, memory and mood) and oncogenesis.

Perhaps the most intriguing interaction between CBD and fungal PS lies with T-lymphocytes. Fungal PS activate the Th1 arm of lymphocyte activity. CBD suppresses certain aspects of lymphocyte activity. CBD primarily induces apoptosis by activating the ER-mediated ROS pathway in primary lymphocytes. This yields a net anti-inflammatory effect and is considered to be the mechanism of the anti-arthritic effects of the compound. The full scope of CBD's effects on immune function is still being characterized, and appears to be context-dependent (specifically, receptor density and target cell population).

CBD has additional pharmacological characteristics, including activity at TRPV1 (involved in nociception) and 5-HT1A. The latter suggests a natural pairing with neurologically active and seratonergic mushrooms species like *Hericium erinaceus* or *Ganoderma lucidum*. CBD has been researched for neuroprotective activities, and is a known antipsychotic, anxiolytic and antidepressant. CBD has also been studied for a very wide range of anticancer actions, including induction of apoptosis (via activation of capsase 3, 8 and 9), antiproliferative activity, anti-angiogenesis and prevention of tumor migration and invasion. At high doses (1 g/day), CBD has demonstrated antineoplastic effects in vitro.

CBD appears to round out and complement the effects of mushroom based ingredient on immune function.

REFERENCES/KEY READING

Cabral G A, Rogers T J and Lichtman A H. Turning Over a New Leaf: Cannabinoid and Endocannabinoid Modulation of Immune Function. *Journal of Neuroimmune Pharmacology,* 10(2):193-203 (2015).

Hassan S, Eldeeb K, Minns P J, Bennett A J, Alexander S P H and Kendall D A. Cannabidiol enhances microglial phagocytosis via transient receptor potential (TRP) channel activation. British *Journal of Pharmacology,* 171(9): 2426-2439 (2014).

Kaplan B L F, Springs A E B and Kaminski N E. The Profile of Immune Modulation by Cannabidiol (CBD) Involves Deregulation of Nuclear Factor of Activated T Cells (NFAT). Biochemical pharmacology, 76(6): 726-737 (2008).

Example 13

Captive honey bees (*Apis mellifera*) were presented with sugar water (typically 50% sugar (sucrose or corn syrup) and 50% water), to which a percentage, based on mass, of mycelial extracts were added at varying concentrations. The net total overall viral pathogen particle counts of bees receiving mycelium extracts in their sugar water at 0.1% and 1%, showed a dose-dependent reduction in overall bee viruses after one week of treatment. The ethanol-water extracts were made using the methods previously described in U.S. Pat. No. 8,765,138 and U.S. patent application Ser. No. 14/641,432. Viral counts were conducted using assays described in U.S. patent application Ser. No. 14/641,432: "Integrative fungal solutions for protecting bees" filed Mar. 8, 2015. The viruses screened included chronic paralysis virus (CPV), acute bee paralysis virus (ABPV), Israeli acute paralysis virus (IAPV), Kashmir bee virus (KBV), black queen cell virus (BQCV), cloudy wing virus (CWV), sacbrood virus (SBV), deformed wing virus (DWV), Kakugo virus, invertebrate iridescent virus type 6 (IIV-6), Lake Sinai viruses (LSV1 and LSV2) and tobacco ringspot virus (TRSV). The ethanol-water extracts from the mycelia of the following species showed a net decrease of virus by 9% for *Trametes versicolor* at 10% concentration, 56% for *Fomitopsis* pinicola at 1% concentration, 68% for *Fomes fomentarius* at 1% concentration, 72% for *Inonotus obliquus* at 1% concentration, and 87% for *Ganoderma lucidum* (=*Ganoderma lucidum* var. *resinaceum*) at 0.1% concentration whilst the Rice Control Extract showed a 63% increase in the viral load at 1% concentration in the same week. Replicated trials were run side-by-side at the same time in the same room for accurate comparisons. The inventor suggests that the antiviral molecules described in this patent may be useful for lessening pathogenic viruses in bees and are within the scope of these inventions. Moreover, since the tobacco ringspot virus is a plant virus that also harms bees, the antivirals described herein may be useful for combating viruses that harm plants.

Example 14

*Lactobacillus acidophilus* and Bifidobacteria can be combined with the mycelium, APIs, or with extracts of the mycelium containing the APIs listed herein, to increase efficacy of the antiviral components described by the inventor and increase bioavailability, facilitate absorption and catalyze forms to increase activity and benefits to hosts challenged with viral pathogens. Moreover, *Trametes versicolor* (Turkey Tan) and *Ganoderma lucidum* (Reishi) are prebiotics favoring beneficial bacteria in the microbiome. As such, these and other beneficial bacteria can be grown with or upon *Trametes versicolor* and *Ganoderma* species mycelium. Hence these combinations can used to help facilitate bacterial activation and complex quorum sensing that can improve the efficacy of the APIs listed herein, improving benefits to the virus host organism.

Example 15

Any of the active principal ingredients or compositions containing these aforementioned APIs that would be diminished through oxidization can be taken with monoamine oxidase (MAO) inhibitors to help maintain antiviral efficacy. Using oxidase inhibitors will allow better survival of the original APIs through the cytochrome P450 pathways especially via the liver. Numerous natural sources of MAO's can be utilized in combinations with the APIs, with the extracts of mycelium containing these APIs, or with other compositions containing these APIs to increase bioavailability, passage or potency. Plants that can be utilized include but are not limited to *Glycyrrhiza giabra* (licorice root), *Acacia catechu* (*catechu* plant), *Ginkgo biloba* (*ginkgo*) Leaf, *Passiflora incarnata* (passionflower) Plant, *Peganum harmala* (Syrian rue) root and seed, *Curcuma longa* (turmeric) root, *Piper methysticum* (kava root), *Hypericum perforatum* (St. John's wort), and *Banisteriopsis caapi* (yage).

Example 16

Various methods can be utilized to increase the production of antivirals from growing mycelium in vitro, within enclosed laboratories, reducing new drug discovery and commercialization costs.

As fungi rot wood, breaking down lignin, they also weep water, rich in p-coumaric acid and other nutraceutical compounds. The more p-coumaric acid, the more laccases (enzymes that degrade lignocellulose) are expressed by the mycelium, the more the wood rots, the more fungal polysaccharides (sugars) are produced and ultimately the more these compounds will be in the fungal exudates. Once UV light stimulates the process of signaling the mycelium into primordia formation, laccases decrease and p-coumaric acid degrades into p-hydroxybenzoic acid, which is closely related to vanillic acid and its metabolic precursors and products.

Interestingly, many of the grains preferred for mycelial spawn production for mushroom industry (see *Growing Gourmet & Medicinal Mushrooms* by the inventor, Paul Stamets, 1993, 2000, Ten Speed Press, Berkeley) are also rich sources of p-coumaric acid and may be useful in antiviral compositions. The primary phenolic acids in rice grain were identified as p-coumaric acid, ferulic acid, and sinapinic acid. Hence rice is a good feedstock substrate upon which to grow mycelium to produce the novel antivirals the inventor has discovered.

p-Coumaric acid is not only in the grains preferred for mushroom spawn production but is also generated during the normal life cycle of mushrooms, especially prior to primordia formation. p-Coumaric acid is a potent inhibitor of tyrosinase, the enzyme essential for melaninization. The presence and abundance of p-coumaric acid interferes with the production of darkly colored pigments. Ultraviolet light stimulates the photodecomposition of p-coumaric acid, enabling melanization and triggering primordia formation. Once UV light stimulates the process of signaling the mycelium into primordia formation, laccases decrease and p-coumaric acid degrade into p-hydroxybenzoic acid, which is closely related to vanillic acid, and other compounds such as ethyl vanillin, caffeic acid, protocatechuic acid, trans-cinnamic acid, ferulic acid, gallic acid, ellagic acid, lanosterol, inotodiol, trametenolic acids, hispolons (hispidins), hispidin, hypholomine B, inoscavin A, davallialactone, phelligridin D, ergosterols, chrysin, cordycepin, trans-coumaric acid, ellagic acid dihydrate, linoleic acids, trans-ferulic acid, gallic acid hydrate, hexanal, 4-hydroxybenzoic acid, p-hydroxybenzaldehyde, p-hydroxybenzoic acid, quercetin hydrate, rutin hydrate, (including related flavonoid glycosides), shikimic acid, syringic acid, acetovanillone, guaiacol, eugenol, sulphurenic acid, dehydrosulphurenic acid, eburicoic acid, stigmasterol and beta-sitosterol, including but not limited to other polyphenols and their congeners that are described herein.

Light stimulation also triggers the production of psilocybin and psilocin in the mycelium of, for instance *Psilocybe cyanescens, Psilocybe cubensis* and *Psilocybe cyanescens*. The "off/on" production of psilocybin, psilocin, baeocystin, nor-baeocystin and other associated alkaloids from the mycelium caused by light exposure (particularly UV) are interrelated to the production of p-coumaric acid and the resultant metabolic expression of tyrosinase coding for melanin, especially prior to, during and after the time of primordia formation. Hence, this inventor suggests that psilocybin, psilocin, baeocystin, nor-baeocystin and other associated alkaloids may have medicinal properties key to the production of novel antivirals not yet discovered by science but predicted by this inventor. Animals such as humans and bees might benefit from using the mycelium of psilocybin producing mushrooms as a source for novel medicinal agents.

As an example, but not one of limitation, the mycelium of *Auricularia auricula* (*A. auricularia-judae*), when grown in culture is whitish and lacks melanin but contains p-coumaric acid. When the mushroom mycelium is exposed to light, the mycelium bio-transforms to create dark brown fruitbodies, which are higher in melanin as they mature, with p-coumaric acid, an inhibitor of melanin, concurrently declining. This is one example and is a strong argument for the benefit of using lightly colored to yellowish mycelium, pre-melaninization, and often rich in mycoflavonoids, as a source of mycelium for making antiviral extracts due to its innate p-coumaric acid content compounded by the native content of p-coumaric acid in the grains that are used for spawn production for growing mycelium. Interestingly, the ideal interface for capturing the best benefits from mycelium for its nutraceutical and p-coumaric acid contents is a short window, often of just a few days in length, before and directly after light exposure, but before dark colored fruitbody development beyond the white primordial stage.

Exposing mycelium grown on rice to blue light (ultraviolet, UV) in the 280-420 nanometer wavelengths, for a short window of time, lasting for a short duration of only 1-5 days, can help create and potentiate the antiviral agents described herein. The intensity of light can range from 50-1,000 lux. By incubating the sterilized rice being actively colonized by the mycelium in plastic bags, which have grown out for a minimum of 1 week and up to 16 weeks, UV light exposure lights can be placed directly above and below horizontally shaped bags for maximum light exposure. The plastic bags can be selected for allowing these blue light wavelengths to reach the mycelium. The mycelium can undergo a phase-change in response to light stimuli into producing derivative antiviral agents that are mentioned in this invention (it is to be expected that during this transitional period, the mycelium may contain varying mixtures of antivirally active compounds). This method and derivative improvements can potentiate the production of antiviral molecules, some of which are intermediates during the melanization pathways activated by light exposure at specific wavelengths. This opens possibilities for customizing the output of specific antiviral molecules using precise wavelengths, exposure times and intensities of light for manufacturing and potentiating antiviral production from mycelium. Lights can be pulsed and/or sequenced with varying wavelengths for exposing mycelium. The mycelium can also be subsequently agitated to cause new growth spurts, causing differentiation of hyphae with multiple nuclei per cell and hyper-expression of extracellular metabolites containing these antivirals. Moreover, antivirals may be emitted differentially over time, allowing for windows of harvesting by washing the mycelium using cold EtOH and $H_2O$ or other solvents and processes known to the art of natural product extraction.

Moreover, the production of active principle ingredients against viruses from mycelium can be additionally enhanced by vibrational actions, including but not limited to pulsed sonic vibration—sonification—in combination with API stimulating UV wavelengths. Specific UV spectra and vibrations can be customized for enhancing antiviral yields. Additionally, combinations of fungi, bacteria and plants (algae) may be utilized. Guilds of fungi, bacteria and plants (algae, in particular) can be orchestrated to create a quorum emitting antiviral and antimicrobial compounds useful in medicine. The interplay of these organisms in concert will elicit novel immune modulators and antiviral compounds useful in medicine. As genomic science evolves, quorums of organisms can be designed specifically to better medically benefit the individual from these and related antivirals based upon the genomic 'personality' or constitution of that individual.

Compounds or extracts from mycelium could induce viral replication of bacteriophages in the microbiome that might help support the discovery of selective yet indirect action against pathogenic bacteria and viruses. In addition to mycelium producing small molecules that directly inhibit viral replication, the mycelium may also produce compounds that rally specific viruses against pathogenic bacteria; modulate bacteria (and indirectly viruses) through quorum sensing induction or inhibition; and select for bacteriophages that may result in antibacterial effects without those components actually testing positive for antibacterial activity in the absence of bacteriophages.

No limitations with respect to the specific embodiments and examples disclosed herein are intended or should be inferred, as the examples and embodiments are representative only. While examples and preferred embodiments of the present invention have been shown and described, it will be apparent to those skilled in the art, or ascertainable using no more than routine experimentation, that many changes and modifications may be made without departing from the invention in its broader aspects. The appended claims are therefore intended to cover all such changes, modifications and equivalents as fall within the true spirit and scope of the invention.

[1] Proietti F A and Carneiro-Proietti A B, Catalan-Soares B C and Murphy E L, Global epidemiology of HTLV-I infection and associated diseases, *Oncogene,* 24(39): 6058-68 (2005).

[2] Aoki, M., T. Motomu, A. Fukushima, T. Hieda, S. Kubo, M. Takabayashi, K. Ono, and Y. Mikami, Antiviral substances with systemic effects produced by Basidiomycetes such as *Fomes fomentarius, Bioscience, Biotechnology, and Biochemistry.* 57(2): 278-293 (1993).

[3] Piraino, F., & C. R. Brandt, Isolation and partial characterization of an antiviral RC-183, from the edible mushroom Rozites caperata, *Antiviral Research* 43: 67-78 (1999).

[4] Sarkar, S., J. Koga, R. J. Whitley, & S. Chatterjee, Antiviral effect of the extract of culture medium of *Lentinula edodes* mycelia on the replication of herpes simplex virus 1, *Antiviral Research,* 20(4): 293-303 (1993).

[5] Collins, R. A. and T. B. Ng, Polysaccharopeptide from *Coriolus versicolor* has potential for use against human immunodeficiency virus type 1 infection, *Life Sciences,* 60: 383-387 (1997).

[6] Brandt, C. R. and F. Piraino, Mushroom antivirals, *Recent Research Developments for Antimicrobial Agents and Chemotherapy,* 4: 11-26 (2000).

[7] Stamets, P., New anti-viral compounds from mushrooms, *HerbalGram.* 51: 24-27 (2001).

[8] Stengler, M., The Health Benefits of Medicinal Mushrooms, p. 6, Basic Health Publications, 2005.

[9] Li et al., Complete mitochondrial genome of the medicinal mushroom *Ganoderma lucidum, PLoS ONE* 8(8):e72038 (2013).

[10] Seong-Kug Eo, Young-So Kim, Chong-Kil Lee and Seong-Sun Han, Antiviral activities of various water and methanol soluble substances isolated from *Ganoderma lucidum, Journal of Ethnopharmacology* 68 (1-3): 129-136 (1999).

[11] Stamets, P., Novel antimicrobial from mushrooms, *HerbalGram* 54: 28-32 (2002).

[12] Stamets, Supra note 7, at 24, 27.

[13] Katayama S, Ohno F, Yamauchi Y, Kato M, Makabe H, Nakamura S, Enzymatic synthesis of novel phenol acid rutinosides using rutinase and their antiviral activity in vitro, *J. Agric. Food Chem.,* 61(40): 9617-22 (Epub 2013 September 25).

[14] *Vanilin*, OECD SIDS, UNEP Publications, p. 9 (1996).

I claim:

1. A method for treating a pathogenic virus infection comprising: administering about 0.1 g to about 2.0 g per day of an antiviral compound comprising syringic acid, trans-cinnamic acid, trans-ferulic acid, or salts thereof to a patient suffering from a viral replication of human Papillomavirus (HPV);

wherein syringic acid, trans-cinnamic, acid and trans-ferulic acid have an antiviral effect Selectivity Index 50 ($SI_{50}$)≥10 against the human papillomavirus (HPV).

2. The method of claim 1, wherein syringic acid has an antiviral effect Selectivity Index 50 ($SI_{50}$)≥30 against the human papillomavirus (HPV); and trans-cinnamic acid and trans-ferulic acid have an antiviral effect Selectivity Index 50 ($SI_{50}$)≥100 against the human papillomavirus (HPV).

3. The method of claim 1, wherein the antiviral compound additionally has an antibacterial effect.

4. A method for treating a pathogenic virus infection comprising: administering a dose of an antiviral composition comprising about 0.1 g to about 2.0 g per day of syringic acid, trans-cinnamic acid, trans-ferulic acid, or salts thereof for a period of time from 10 to 60 days to a patient suffering from a viral replication of human Papillomavirus (HPV);

wherein syringic acid, trans-cinnamic acid, and trans-ferulic acid have an antiviral effect Selectivity Index 50 ($SI_{50}$)≥10 against the human papillomavirus (HPV).

5. The method of claim 4, wherein the dose is about 0.1 to 1.5 grams per day.

6. The method of claim 4, wherein the dose is about 0.25 to 1.4 grams per day.

7. The method of claim 4, wherein the dose is about 1,000 mg per day.

8. The method of claim 4, wherein syringic acid has an antiviral effect Selectivity Index 50 ($SI_{50}$)≥30 against the human papillomavirus (HPV); and trans-cinnamic acid and trans-ferulic acid have an antiviral effect Selectivity Index 50 ($SI_{50}$)≥100 against the human papillomavirus (HPV).

9. The method of claim 4, wherein the composition additionally has an antibacterial effect.

10. A method for treating a pathogenic virus infection comprising: administering about 0.1 g to about 2.0 g per day of syringic acid, trans-cinnamic acid, trans-ferulic acid, or salts thereof to a patient suffering from a viral replication of human Papillomavirus (HPV).

* * * * *